(12) United States Patent
Thoemmes et al.

(10) Patent No.: US 8,813,743 B2
(45) Date of Patent: Aug. 26, 2014

(54) ATOMIZER

(75) Inventors: Ralf Thoemmes, Willich (DE); Timo Von Brunn, Berlin (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 1621 days.

(21) Appl. No.: 11/749,259

(22) Filed: May 16, 2007

(65) Prior Publication Data

US 2007/0267015 A1 Nov. 22, 2007

(30) Foreign Application Priority Data

May 18, 2006 (DE) .......................... 10 2006 023 657
Sep. 18, 2006 (DE) .......................... 10 2006 043 637

(51) Int. Cl.
*A61M 11/02* (2006.01)
*A61M 11/00* (2006.01)
*A61M 15/00* (2006.01)

(52) U.S. Cl.
CPC ......... *A61M 11/006* (2014.02); *A61M 15/0048* (2014.02); *A61M 11/02* (2013.01); *A61M 15/0061* (2014.02); *A61M 15/0045* (2013.01)
USPC ............ 128/200.22; 128/203.12; 128/203.15; 128/200.14

(58) Field of Classification Search
CPC ... A61M 11/00; A61M 11/005; A61M 11/02; A61M 11/04; A61M 11/041; A61M 11/06; A61M 11/08; A61M 15/00; A61M 15/0028; A61M 15/0045; A61M 15/0065; A61M 15/0085; A61M 15/009; A61M 15/0091; A61M 15/02; A61M 15/06; A61M 15/08; A61M 2015/0021; A61M 2015/0025; A61M 2015/0026; A61M 2015/0033; A61M 2015/0048; A61M 2015/005
USPC ............ 128/200.24, 203.12, 203.15, 203.19, 128/203.21; 222/167–172; 604/58, 63
See application file for complete search history.

(56) References Cited

U.S. PATENT DOCUMENTS

| | | | |
|---|---|---|---|
| 5,533,502 A | 7/1996 | Piper | |
| 6,179,164 B1 * | 1/2001 | Fuchs | 222/82 |
| 6,725,857 B2 | 4/2004 | Ritsche | |
| 6,752,147 B1 * | 6/2004 | Goldemann et al. | 128/203.15 |
| 6,810,873 B1 * | 11/2004 | Haikarainen et al. | 128/203.15 |
| 6,880,555 B1 * | 4/2005 | Brunnberg et al. | 128/203.12 |
| 7,032,594 B2 * | 4/2006 | Newton et al. | 128/203.15 |
| 7,275,537 B2 * | 10/2007 | Nelson et al. | 128/203.15 |
| 7,434,579 B2 * | 10/2008 | Young et al. | 128/203.15 |
| 2002/0040713 A1 * | 4/2002 | Eisele et al. | 128/203.21 |
| 2003/0172927 A1 * | 9/2003 | Young et al. | 128/203.15 |

(Continued)

FOREIGN PATENT DOCUMENTS

WO 91/06333 A1 5/1991

*Primary Examiner* — Valerie L Skorupa
(74) *Attorney, Agent, or Firm* — Robert Mlotkowski; Safran & Cole, P.C.; David S. Safran

(57) ABSTRACT

An atomizer for the delivery, and in particular, the atomization of a formulation, particularly, a powder. A simple construction and simple intuitive operation are made possible, in particular, by the fact that the atomizer has a mouthpiece with an associated cover, so that opening and/or closing of the cover causes a delivery medium, in particular air, to be taken in and/or put under pressure by a delivery device, a spring store is put under tension and/or a preferably annular reservoir containing a plurality of doses of the formulation is further rotated.

27 Claims, 33 Drawing Sheets

(56) References Cited

U.S. PATENT DOCUMENTS

| | | |
|---|---|---|
| 2003/0183230 A1* | 10/2003 | Nelson et al. ............ 128/203.15 |
| 2004/0025877 A1* | 2/2004 | Crowder et al. ......... 128/203.15 |
| 2004/0035420 A1* | 2/2004 | Davies et al. ............ 128/203.15 |
| 2005/0103337 A1* | 5/2005 | Hickey et al. ............ 128/203.15 |
| 2007/0221218 A1* | 9/2007 | Warden et al. ........... 128/203.15 |
| 2008/0202515 A1* | 8/2008 | Hodson et al. ........... 128/203.21 |
| 2009/0139516 A1* | 6/2009 | Augustyn et al. ........ 128/200.23 |

* cited by examiner

ATOMIZER

BACKGROUND OF THE INVENTION

1. Field of the Invention

The present invention relates to an atomizer for delivering a formulation in particular from a reservoir having a plurality of preferably annularly arranged receptacles, each of which contains a dose of the formulation.

2. Description of Related Art

The present invention relates, in particular, to the delivery and atomization of a formulation for inhalation or for other medical or therapeutic purposes. Particularly preferably, the present invention relates to the delivery of medical, pharmaceutical and/or therapeutic formulations which in particular contain or consist of at least one active substance.

The present invention relates in particular to an inhaler. During atomization, an aerosol or a spray cloud is produced having, particularly for inhalation, very fine, solid and/or liquid particles, preferably in the range from 1 to 10 µm.

The formulation is preferably a powder. Particularly preferably, the invention relates to a powder inhaler. The term "formulation" according to the present invention preferably also includes liquids, however, while the term "liquid" is to be understood in a broader sense as including inter alia solutions, suspensions, solutions (mixture of solution and suspension), dispersions, mixtures thereof or the like.

The specification that follows is directed primarily to the delivery and atomization of a powdered formulation or to a powder inhaler, even if the invention is not restricted thereto, but may also be used, in particular, for other inhalers, atomizers or dispensers.

The present invention relates in particular to an atomizer with a pre-metered formulation. In particular the individual doses are contained in separate receptacles such as chambers, blister pouches, inserts, capsules or the like, and can be individually taken out and atomized.

Basically, there are passive and active atomizers. In the passive type, the formulation is expelled through the air current produced by the user on inhaling or breathing in. In the active type the formulation is expelled independently of the breathing in during inhaling, and the delivery can be triggered by the inhalation process—in particular by so-called breath triggering. In particular, a current of a delivery medium such as air or some other gas is generated by the atomizer or inhaler itself in order to deliver the formulation. For this purpose, the atomizer has a delivery device, such as an air pump or a pressurized gas container. The advantage of the active type over the passive type is that, in the active type, a very easily reproducible delivery and atomization of the formulation can be achieved independently of the user.

European Patent EP 0 950 423 B1 and corresponding U.S. Pat. No. 6,179,164 disclose an active dispenser for media, particularly powders, with a compressed air pump, namely a piston pump, integrated in the dispenser. The dispenser has a blister disc with blister pouches containing the powder arranged in a circle. To actuate or open the individual blister pouches the housing part is moved axially.

European Patent EP 1 132 104 B1 and corresponding U.S. Pat. No. 6,725,857 disclose an active dispenser for delivering a medium containing at least one pharmaceutical active substance from a blister strip. The dispenser has a pump for a fluid, particularly air, for expelling the medium, an impact spike for creating a fluid connection between the pump and a blister pouch and a lateral actuating device which when actuated both positions a blister pouch in relation to the impact spike and also brings about the expulsion of the medium. The dispenser also has a spring which is under tension during a first actuating step and can be released into a relaxed position during a second actuating step by releasing a latch, the spring successively causing the blister pouch to be positioned in relation to the impact spike, the blister pouch to be opened by the impact spike and air to be supplied to the blister pouch in order to expel the medium.

International Patent Application Publication WO 91/06333 A1 discloses an active dispenser having a hollow cylindrical reservoir comprising a plurality of axially extending chambers containing powder. By axially pushing the dispenser together air is compressed in a piston pump and is finally conveyed through the respective chamber in order to expel the respective dose of powder.

U.S. Pat. No. 5,533,502 discloses a passive powder inhaler having an annular reservoir, particularly a blister, having a plurality of receptacles for powder. The reservoir is rotatably held in the inhaler by a carrier. The carrier can be rotated by means of an axially protruding knob to select the next receptacle and can be moved axially in order to pierce the receptacle. However, this does not allow easy operation. In fact, the user has to hold the knob or carrier in the axially displaced state during inhalation. After being released, the carrier with the reservoir returns to its axial starting position away from the piercing elements by the effect of spring force.

SUMMARY OF THE INVENTION

A primary object of the present invention is to provide an atomizer which can be operated very simply, particularly intuitively, while being simple and inexpensive in its construction, and/or which has a compact structure, particularly a low overall height.

The problem stated above is solved by an atomizer for delivering a formulation in particular from a reservoir having a plurality of preferably annularly arranged receptacles, each of which contains a dose of the formulation, as described in greater detail below.

According to a first aspect of the present invention, the covering of the mouthpiece of the atomizer is coupled to a delivery device, such as a pump, and/or an energy store, such as a spring store, such that opening and/or closing the cover actuates the delivery device and/or generates energy and this is stored in the energy store. In particular, when the cover is opened, a delivery medium, preferably air, is taken in by the delivery device and/or placed under pressure. Alternatively or additionally, energy produced by opening and/or closing of the cover is preferably stored by tensioning the spring store. Thus, a very simple and in particular intuitive operation of the atomizer is made possible. Furthermore, this enables the construction to be kept particularly simple and hence also inexpensive. For example, there may be no need to have a separate actuating element for operating the delivery device or pump and/or for tensioning the spring store or the like.

According to a second aspect of the present invention which can also be implemented independently, the atomizer has a gear or transmission for producing, from the opening and/or closing movement of the cover, a preferably axial movement to open the next receptacle, for displacing and/or advancing the store by one receptacle, for tensioning a spring store, for actuating a delivery device, particularly for taking in air, and/or for actuating a counter or other device of the atomizer. This results in a simple, compact construction, particularly when the gear or transmission is arranged within an annular arrangement of the reservoir or receptacles.

In a third aspect of the present invention which can also be implemented independently, the atomizer has a closable chamber for accommodating medicaments independently of the reservoir. This results in a simple, compact construction with increased medicament capacity.

Further aspects, features, properties and advantages of the present invention will become apparent from the following description of preferred embodiments, with reference to the accompany drawings.

DETAILED DESCRIPTION OF THE INVENTION

Figure 1:
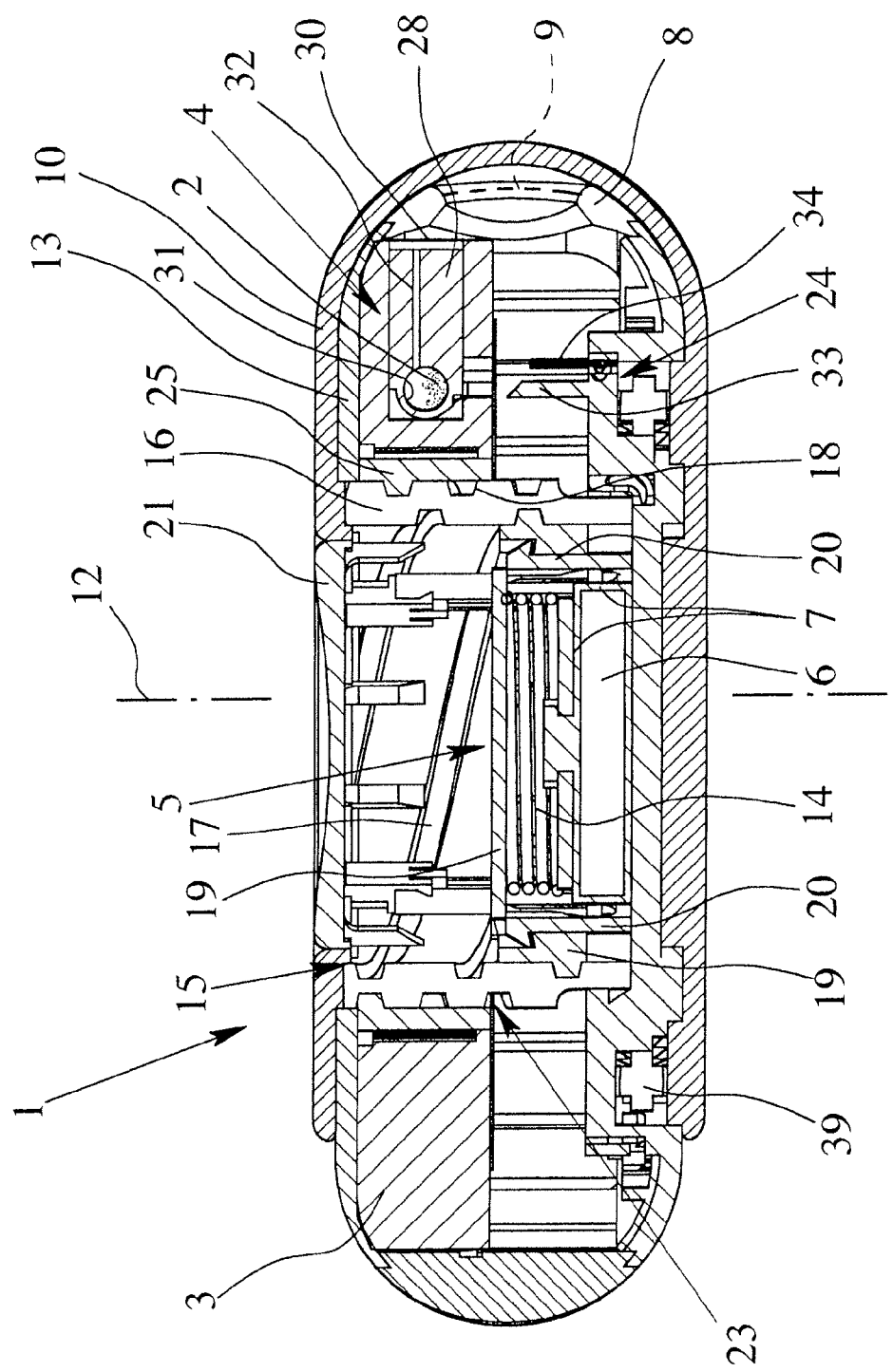
FIG. 1 is a schematic cross section of an atomizer according to a first embodiment in a transportation position.

In the Figures, the same reference numerals have been used for identical or similar parts, even if the associated description has not been repeated. In particular, the same or corresponding advantages and properties are obtained thereby.

FIG. 1 shows in schematic section a proposed atomizer 1 according to a first embodiment in the transportation position. In particular, it is a preferably portable inhaler, particularly preferably, for aerosol therapy.

The atomizer 1 is designed to deliver and atomize a formulation 2, preferably powder. In particular, the atomizer 1 can be used for a formulation 2 in the sense explained above.

The formulation 2 is preferably pre-metered into individual doses which can be delivered one after another by the atomizer 1, particularly for inhalation.

The atomizer 1 has a reservoir 3 or is designed to hold one. If necessary, the reservoir 3 can be inserted in the atomizer 1, and optionally, replaced for repeated use of the atomizer 1.

The reservoir 3 has a plurality of receptacles 4, each containing one dose of the formulation 2. The receptacles 4 may be, e.g., blister pockets, but preferably, contain inserts 28 with the respective dose of the formulation 2. The reservoir 3 is preferably made of a rigid and/or annular construction. In particular, the reservoir 3 or the receptacles 4 form an annular arrangement, the receptacles 4 preferably being distributed around the circumference of the reservoir 3.

The atomizer 1 is preferably of the active type. In the embodiment shown by way of example, the atomizer 1, preferably, has a delivery device 5 for a delivery medium, particularly air or some other gas, for delivering the formulation 2. The delivery device 5 is constructed, in particular, as a pump, particularly preferably, an air pump, or is designed in some other way to convey the delivery medium.

In particular, the delivery device 5 has a pump chamber 6 which is preferably formed, delimited and/or variable by a bellows 7 and/or some other element of the delivery device 5.

Using the delivery device 5 ambient air, in particular, can be taken in as the delivery medium and put under pressure. Using the delivery medium the formulation 2, i.e., a dose of the formulation 2 can be expelled from a receptacle 4 on actuation or use of the atomizer 1, in particular, only after it has been triggered accordingly. However, the delivery device 5 may theoretically also produce, provide and/or pressurize air, other gas or even liquid as the delivery medium in some other way, so as to be able to deliver the formulation 2, particularly, as an aerosol or spray mist with preferably fine particles (solid and/or liquid).

The atomizer 1 preferably has an end piece or mouthpiece 8 for delivering the formulation 2, in particular, to a user or patient. From now on, only the term "mouthpiece" will be used for convenience; however, use of this term is not intended exclude the use of some other end piece for administering or delivering the formulation 2, particularly when the atomizer 1 is not used as an inhaler.

A delivery opening of the mouthpiece 8 is optionally provided with a grid 9 or other protective element, particularly in order to be able to prevent damage to the atomizer 1, e.g., of the reservoir 3 or receptacles 4, caused by external effects or the like, and/or to prevent the expulsion of other parts, larger particles or the like.

Figure 2:
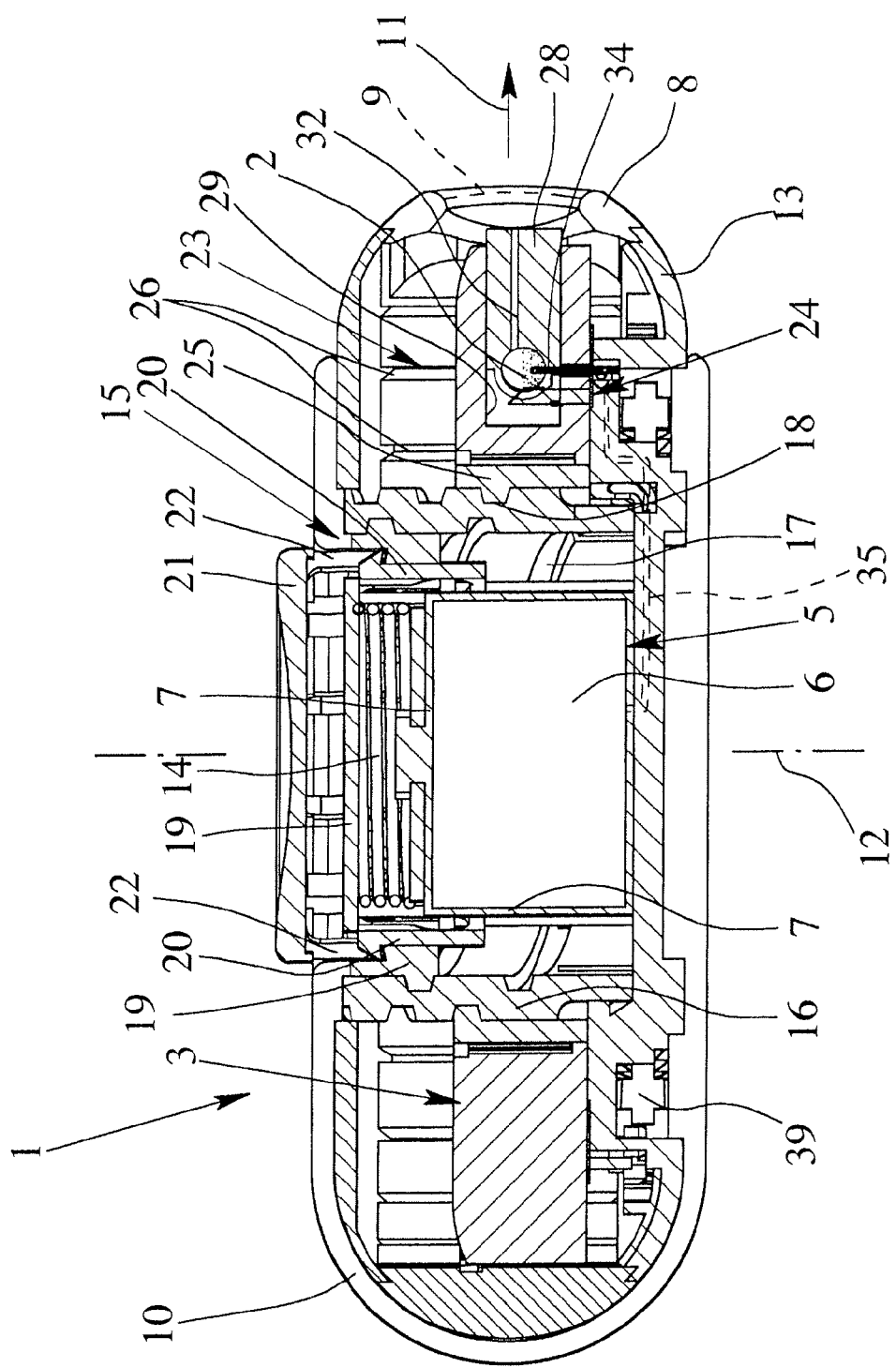
FIG. 2 is a schematic cross section of the atomizer of FIG. 1 in an activated state.

The atomizer 1 preferably has a cover 10 associated with the mouthpiece 8, which is manually movable, in particular, to enable the mouthpiece 8 to be opened and closed. FIG. 1 shows the cover 10 in the closed state, i.e., covering the mouthpiece 8. FIG. 2 shows, in a similar sectional view, the activated atomizer 1, i.e., the atomizer 1 ready for inhalation, with the cover 10 open, i.e., the mouthpiece 8 freely accessible.

The cover 10 is movable, in particular, at right angles to the delivery direction 111 indicated in FIG. 2, in particular, slidably and/or pivotably.

In the embodiment shown, the cover 10 is preferably pivotable or rotatable about a central axis 12 of the atomizer 1 or the annular arrangement of the reservoir 3 or the receptacles 4 or a rotation axis of the reservoir 3. The atomizer 1 or its housing 13 is preferably at least substantially rotationally symmetrical, particularly relative to the axis 12, and/or constructed to be at least substantially flat or disc-shaped, in particular, substantially in the form of a circular disc. However, other geometric and constructive solutions and arrangements are also possible.

The cover 10 is preferably movable at a tangent to the housing 13 of the atomizer 1 or along a periphery of the atomizer 1. The cover 10 extends, in particular, substantially peripherally, in particular, along a circumferential section of the atomizer 1.

FIG. 3 shows a preferred construction, particularly a flat, disc-shaped and/or round embodiment of the atomizer 1. It is also apparent that the cover 10 covers or overlaps a circumferential portion of the atomizer 1 of, preferably, at least 90°, in particular, substantially about 150° to 170°, particularly, both in the peripheral direction and also from one flat side through the circumferential portion to the other. However, here again, other constructive solutions and configurations are also possible.

In the fully opened position shown in FIGS. 2 & 3, in the embodiment shown, the cover 10 is preferably rotated or pivoted through about 150° to 180° relative to the closed transportation position shown in FIG. 1. However, other pivot angles are also possible.

Alternatively, the cover 10 may be formed, for example, in the manner of a slide and/or shutter and may be guided, mounted or held, for example, by the housing 13 or mouthpiece 8.

The cover 10 is preferably coupled to the delivery device 5 such that, by opening and/or closing, and in particular, simply by opening the cover 10, the delivery device 5 is operated or actuated, and in particular, the delivery medium (particularly ambient air) is taken in by the delivery device 5. Alternatively or additionally, the delivery medium can be put under pressure by the opening and/or closing movement of the cover 10. In this case, operation is very simple and intuitive, as the actuation of the delivery device 5 is intuitively effected by opening and/or closing the cover 10, and in particular, there is no need for any additional actuation of any other actuating element.

The atomizer 1 or delivery device 5, preferably, has an energy store, particularly a spring store, in the form of a spring 14 in the embodiment shown. The cover 10 is preferably coupled to the energy store such that energy is produced by opening and/or closing the cover 10 and is stored in the energy store. In particular, opening and/or closing particularly preferably, just closing—the cover 10 causes energy to be stored by tensioning the spring store or the spring 14.

The energy store or spring store may drive various devices and/or serve different purposes and serves, in particular, to drive the delivery device 5 or to put the delivery medium under pressure or displace it from the pump chamber 6, in order to convey the delivery medium through a receptacle and expel the corresponding dose of the formulation 2 in the desired manner and then atomize it. The delivery medium is preferably only put under pressure during or for the purpose of delivering the formulation 2. However, in theory, this may also take place beforehand, in which case a valve device or the like (not shown) is provided, in particular, to prevent premature delivery of the delivery medium and the formulation 2 before the actual desired delivery and atomization.

The energy store is preferably associated with the delivery device 5 or forms a part thereof. Particularly preferably, the energy store or spring store surrounds the delivery device 5 or is arranged or integrated therein.

In the embodiment shown by way of example, the spring 14 is mounted on an axial extension relative to the direction of the pump or the pumping action or behind the pump chamber 6 or the bellows 7. In this case, the spring 14 preferably acts as a compression spring which compresses or pushes together the pump chamber 6 or the bellows 7 or displaces, for example, a piston (not shown) in order to reduce the size of the pump chamber 6 or compress the delivery medium contained therein—i.e., put it under pressure—and thereby bring about the delivery of the delivery medium.

The delivery device 5 and/or the energy store is or are particularly preferably, arranged inside the annular arrangement of the reservoir 3 or receptacles 4, in particular, thus, at least substantially in the centre of the housing 13. Preferably, the delivery device 5 and the energy store are arranged in the region of the axis 12 or around the axis 12, preferably concentrically thereto.

The arrangement of the delivery device 5 and/or energy store or other devices within the annular arrangement of the reservoir 3 or receptacles 4 according to the invention also enables the delivery device 5 and/or the energy store to extend axially beyond the reservoir 3 or receptacles 4 or, for example, in the transportation position shown in FIG. 1, to be arranged in an axially offset position from the main or annular plane of the reservoir 3.

The arrangement of the delivery device 5 and/or the energy store inside the annular arrangement of the reservoir 3 or receptacles 4 or other devices results in a particularly compact construction and in particular, a particularly low axial height of the atomizer 1.

The pivot axis of the cover 10 preferably corresponds to the axis 12 of the annular arrangement of the reservoir 3 or receptacles 4, the reservoir 3 preferably being rotatable about this axis, as will be described in more detail hereinafter.

The atomizer 1 preferably has a transmission or gear 15, particularly for the above-mentioned preferred coupling of the cover 10 to the delivery device 5 and/or the energy store. Alternatively or additionally, the transmission, named gear 15 in the following, can also drive and/or actuate other devices or perform other functions.

Preferably, the gear 15 is arranged—partly or totally—within the annular arrangement of the reservoir 3 or receptacles 4. This, in turn, contributes to the compact structure of the atomizer 1.

The gear 15 is preferably driven by movement of the cover 10, and in particular, is coupled directly or indirectly thereto.

Particularly preferably, the gear 15 generates, from the opening and/or closing movement of the cover 10, an axial movement, particularly with respect to the annular arrangement and/or the axis 12. Particularly preferably, the axial movement extends on or along the axis 12 or parallel thereto. The term "axial movement" is to be understood as meaning that at least one component of the movement generated by the gear 15 on the power takeoff side extends in the axial direction.

The axial movement that can be generated by the gear 15 is used, particularly preferably, for opening the next receptacle 4, for displacing and/or advancing the reservoir 3 or receptacles 4, for tensioning the spring store, for actuating the delivery device 5, particularly for taking in air, and/or for actuating another device of the atomizer 1, such as a counter. Preferably, the gear 15 has different transmission ratios on the power takeoff side for driving different devices.

The gear 15 preferably comprises at least one thread, particularly, a rotatable threaded sleeve 16 which, particularly preferably, has an internal thread 17 and/or an external thread 18.

The thread or the threaded sleeve 16 is preferably directly or indirectly coupled or connected to the cover 10 and/or arranged coaxially with the pivot axis of the cover 10, or forms the latter. Rotation of the cover 10, in particular, directly causes the threaded sleeve 16 to rotate.

In the embodiment shown, the delivery device 5, and in particular, also the energy store can be driven or actuated by the gear 15, preferably, in the axial direction, in particular, via the internal thread 17. The internal thread 17 preferably engages with an inner engagement member 19 which comprises, in particular, a complementary threaded portion or other projections, engagement surfaces or the like, so that rotation of the threaded sleeve 16 causes axial movement of the non-rotating engagement member 19 associated with the delivery device 5 or the energy store.

In particular, the spring 14 is supported at one end on the engagement member 19, which preferably forms a corresponding spring seat or abutment, e.g., by means of an end plate or the like, and at the other end is coupled to the movable end of the bellows 7 or other pumping element of the delivery device 5. However, once again, different constructional solutions are possible. In particular, the gear 15 or engagement member may also only act directly on the bellows 7 or other pumping element and in addition are coupled to the spring 14 only indirectly or not at all.

Starting from the transportation position shown in FIG. 1, when the cover 10 is opened the engagement member 19 is moved axially on the one hand, i.e., it performs the preferred axial movement while, on the other hand a preferably interlocking and/or releasable connection between the engagement member 19 and the delivery device 5 and/or the spring store—for example, by means of at least one locking arm 20—transmits the axial movement and in particular, causes the pump chamber 6 to enlarge in the axial direction and preferably take in ambient air, the bellows 7 is pulled open or enlarged in the axial direction and/or—particularly when the axial end position is reached—a preferably centrally or axially arranged actuating element 21 is released and/or moved axially out, as shown in the end position in FIG. 2. The tensioned spring 14 is preferably moved axially together with the engagement member 19 and an axial end of the bellows 7.

During subsequent actuation of the actuating element 21, particularly by pressing radially inwards, the delivery is initiated and the formulation 2 is atomized from an adjacent receptacle 4. In particular, the connection between the engagement member 19, on the one hand, and the minimum of one locking arm 20 or the delivery device 5 and/or the energy store, on the other hand, is undone, in particular, by the fact that at least one engaging element 22 springs the at least one locking arm 20 into a non-engaged position (radially inwards in the embodiment shown). The recoil or spring force of the spring store or of the tensioned spring 14 then causes the bellows 7 to be collapsed and the pump chamber 6 to be made smaller, as a result of which the delivery medium (particularly ambient air) contained in the pump chamber 6 is put under pressure and displaced, so that the formulation 2 is expelled and atomized in the desired manner, as will be discussed in more detail hereinafter.

Alternatively or in addition to the thread, theoretically some other control cam, ramp, inclined plane or other geared connected may be used, particularly to achieve the sequence of movements described hereinbefore, a sequence of movements described hereinafter and/or some other sequence of movements.

Preferably, the atomizer 1 has a transporting device 23 to enable the reservoir 3 to be advanced or further rotated preferably stepwise to the next receptacle 4 or by one receptacle 4, and preferably, a connecting device 24 for, in particular, connecting the receptacles 4 singly to the delivery device 5 and/or in particular, for individually opening the receptacles 4.

Preferably, the transporting device 23 and/or the connecting device 24 is driven or actuated by the opening and/or closing of the cover 10, particularly via the gear 15. Particularly preferably, an axial movement generated by the gear 15 is used again.

In the embodiment shown, the actuation of the transporting device 23 and the actuation of the connecting device 24—i.e., the advancing of the reservoir 3 to the next receptacle 4 and the opening of the next receptacle 4 and/or attachment to the delivery device 5—are combined or coupled. However, these actuations may also be controlled independently of one another, or in particular, through separate drives of the gear 15 or separate drive chains.

Preferably, combined driving of the transporting device 23 and connecting device 24 is achieved by means of an external engagement member 25 which engages with the external thread 18 of the threaded sleeve 16—particularly via a corresponding threaded portion, a sliding surface or the like. This engagement member 25 is, in particular, non-rotationally connected to the preferably annular reservoir 3 or is formed thereby. For example, the engagement member 25 may form a closed inner ring of the reservoir 3. However, this is not absolutely necessary. For example, the reservoir 3 may also engage directly with the gear 15, particularly the external thread 18 of the threaded sleeve 16, via corresponding sliding surfaces or the like.

The reservoir 3 is preferably locked at its outer periphery against free rotation with the threaded sleeve 16 or the external thread 18 about the axis 12, in particular, by a sliding guide formed, for example, in collaboration with the housing 13.

Rotating the threaded sleeve 16 or external thread 18 (or other control cam) causes axial movement of the non-co-rotating engagement member 25 and hence of the reservoir 3. For example, the reservoir 3 with the receptacles 4 is moved from the axial position shown in FIG. 1 in the transportation position, during and as a result of the opening of the cover 10—i.e., by means of the gear 15—axially into the position shown in FIG. 2. This axial or lifting movement takes place in the embodiment shown in the opposite direction to the axial movement for actuating the delivery device 5 (particularly taking in the ambient air) but may also go in the same direction.

Only after the actuating element 21 has been actuated—i.e., after the delivery and atomization of the formulation 2 from a receptacle 4—is the cover 10 closed again. Closing the cover 10 and rotating the threaded sleeve 16 causes the reservoir 3 to perform the opposite axial or lifting movement again. In the course of this axial movement and/or during the opposing axial movement during the opening of the cover 10, the sliding guide leads to an advancing or further rotation of the reservoir 3 by one receptacle 4, i.e., to the next receptacle 4.

Figure 4A:
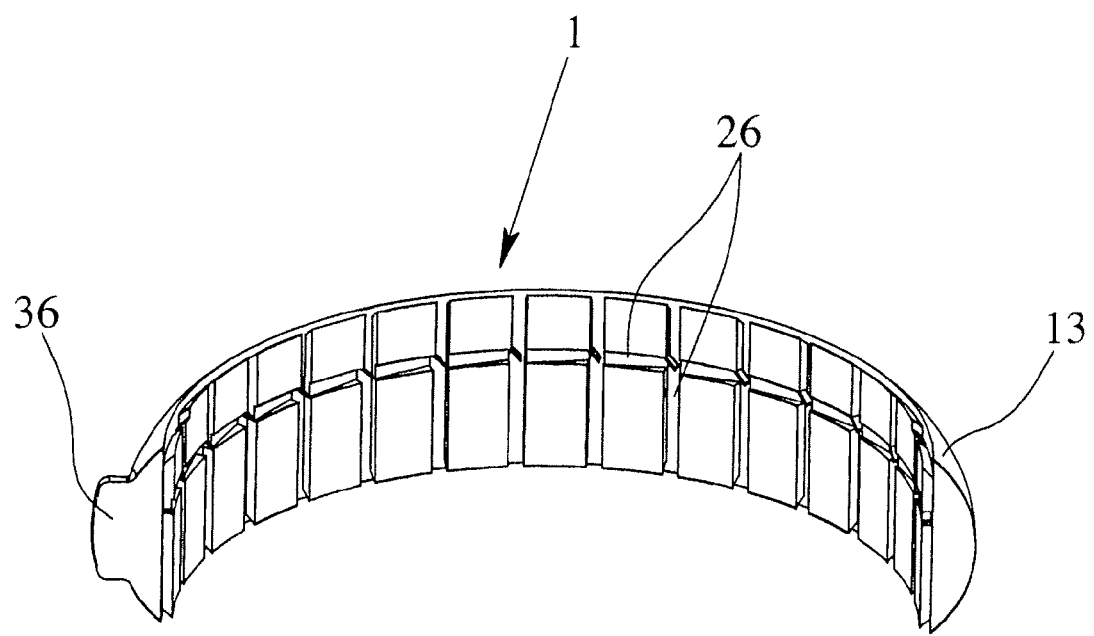
FIG. 4a is a schematic view of a sliding guide of the atomizer according to FIG. 1.

FIG. 4a illustrates a possible constructional configuration of the sliding guide or of a control groove or control cam 26 preferably formed by the inner wall of the housing 13, in order to carry out the desired, preferably alternating axial movement of the reservoir 3 and the stepwise further rotation of the reservoir 3 by a receptacle 4. This combined movement is achieved, in particular, by the alternately axially and diagonally extending portions of the control cam 26, in which a projection of the reservoir 3 engages radially, for example. However, other radially inner and/or axial mechanisms are also possible.

In the embodiment shown, the outer engagement member 25 and the above-mentioned sliding guide form the transporting device 23 or components thereof. In particular, the sliding guide or the transporting mechanism is constructed in the manner of a ballpoint pen mechanism (axial movement back and forth leads to stepwise rotation). However, other constructional solutions are also possible which bring about, in particular, stepwise advancing or further rotation of the reservoir 3 by one receptacle 4—particularly preferably, by the axial movement and/or rotation of a gear component, such as the threaded sleeve 16.

Figure 4B:
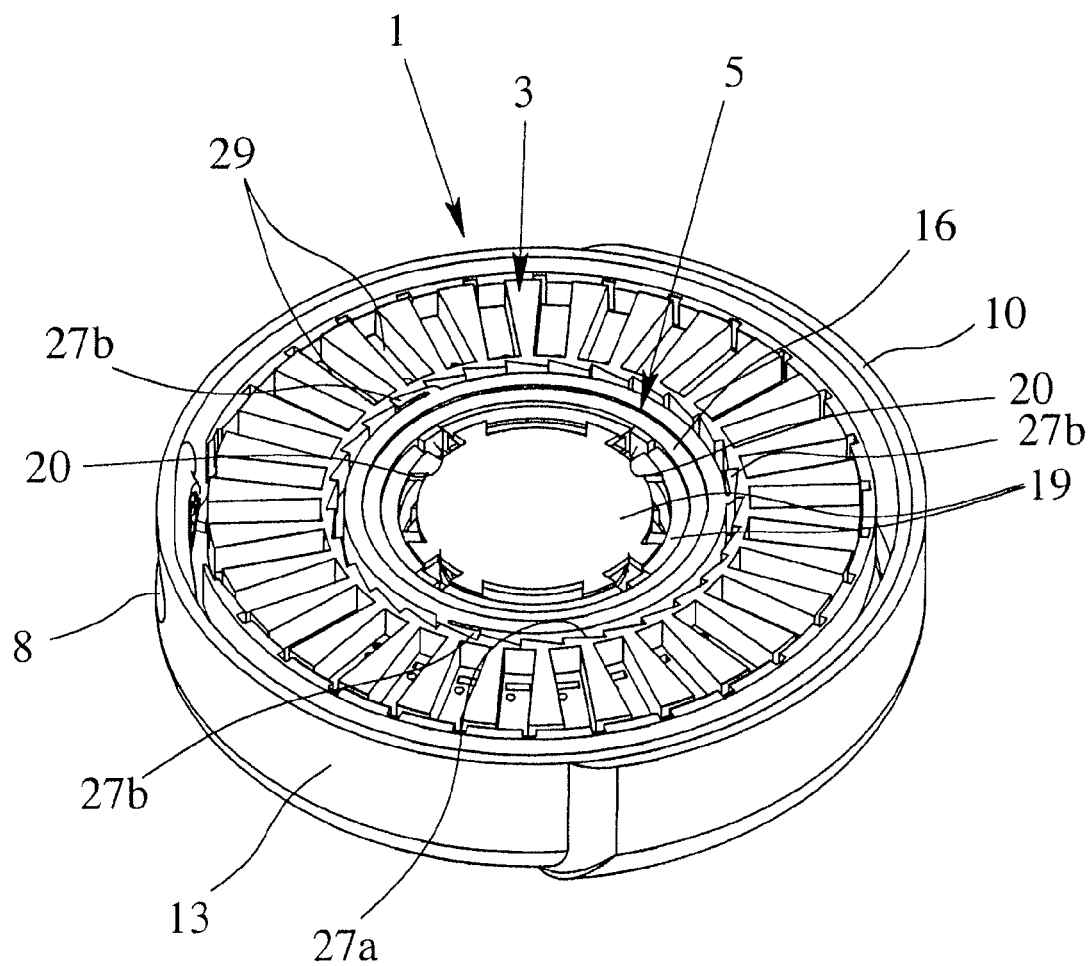
FIG. 4b is a schematic view of the open or cutaway atomizer according to FIG. 1 with a ratchet mechanism.

According to an alternative embodiment shown in FIG. 4b, the transporting device 23 may have, alternatively or in addition to the sliding guide or control cam 26, a ratchet mechanism or locking latch mechanism 27a, 27b which allows an, in particular, stepwise advancing or further rotation of the reservoir 3, which is shown open or cut away in the drawing. The ratchet mechanism 27a, 27b is formed, in particular, between the outer engagement member 25 and the annular reservoir 3, so that these two are rotatable in one direction relative to one another by corresponding ratchet steps.

The ratchet mechanism 27 has, in the embodiment shown, in particular, a ratchet 27a in which a transporting arm 27b can engage. Particularly preferably, radial locking engagement takes place. However, in principle, it may also occur in the axial direction. Preferably, the ratchet mechanism 27 is formed on the inside and/or encircling the reservoir 3. The transporting arm 27b can be moved by the delivery device 5, particularly the gear 15, particularly preferably, in alternating manner. In the embodiment shown, the transporting arm 27b is directly or indirectly connected to the threaded sleeve 16, particularly formed on the outer engagement member 25. Preferably, the transporting arm 27b is biased elastically—particularly by its inherent elasticity—towards the ratchet 27a to produce the desired locking engagement. To obtain the desired reliable stepwise movement of the reservoir 3 by back and forth movement or rotation of the cover 10 or threaded sleeve 16, particularly preferably, a plurality of transporting arms 27b are provided.

A preferred construction of the connecting device 24 will now be described in more detail. However, for ease of understanding, a preferred embodiment of the reservoir 3 will first be explained in more detail.

There are various possibilities for the construction and configuration of the reservoir 3 and receptacles 4. For example, it may be a blister arrangement, optionally combined with a carrier, or the like. The individual receptacles 4 are then formed by blister pouches, for example.

Particularly preferably, the receptacles 4 are formed by inserts 28 which are accommodated in preferably separate, in particular, radially extending guides or receiving chambers 29 of the reservoir 3. In particular, each insert 28 is preferably radially displaceable or movable.

In the embodiment shown in particular, the inserts 28, receiving chambers 29, mouthpiece 8 and/or delivery device 11 are aligned radially. However, theoretically, it is also possible to have a different alignment, for example, axial.

The receiving chambers 29 are preferably provided on the outer periphery of the reservoir 3 or the annular arrangement with openings 30 which are preferably closed, in particular, sealed, or otherwise closed off or covered, when not in use or in the state as supplied. A corresponding sealing, foil, film or the like is indicated by reference sign 30 in FIG. 1. In the state as supplied, the receiving chambers 29 containing the inserts 28 are each hermetically sealed, particularly in fluid tight and possibly also gastight manner. The reservoir 3 is made, in particular, of diffusion proof plastics and/or is optionally provided with a diffusion proof outer packaging.

Each insert 28 has a storage chamber 31 which contains the dose or formulation 2 of the particular insert 28, and in particular, has been filled with the formulation 2 during the manufacture of the reservoir 3 or atomizer 1 at the factory end. Adjoining the storage chamber 31 is preferably a duct or channel 32 in the insert 28 for delivering, atomizing and/or de-agglomerating the formulation 2. The channel 32 may, if required, merge into a nozzle (not shown) or form such a nozzle. In the embodiment shown, the inserts 28 thus form with their storage chambers 31 the receptacles 4 for the formulation 2 or the inserts 28 are accommodated in the receiving chambers 29 or the receptacles 4 formed in or by the reservoir 3.

In order to deliver the formulation 2, the respective receptacle 4 is opened. In the embodiment shown, this is preferably carried out at the delivery end by moving the respective insert 28 partly out of its receiving chamber 29, particularly through the opening 30, and pushing a seal or the like (not shown) preferably radially outwards through it. In this way, the receiving chamber 29 or its opening 30 is opened up and the channel 32 is freed. For example, the sealing foil or the like (not shown) which closes off the respective opening 30 is torn away from the insert 28 or another closure or covering member that closes off the opening 30 is displaced, opened, pushed out or otherwise removed from the insert 28.

The preferred radial displacement of the insert 28 in order to open the respective receiving chamber 29 is carried out in the embodiment shown preferably by means of the connecting device 24 or the transporting device 23, in particular, by having a finger 33 or other actuating member of the connecting device 24 penetrate, in particular, axially into the receiving chamber 29 in the region of the inner radial end of the respective insert 28, and in particular, by a corresponding sliding surface (on the finger 33 and/or insert 28) performing the desired outward radial movement of the insert 28.

The penetration of the finger 33 is possible, for example, because the reservoir 3 has a sufficiently thin wall or frangible point in the region of penetration. Alternatively, the reservoir 3 may also comprise an opening or the like which is sealed, covered or provided with a closure and can be opened or penetrated by the finger 33.

FIG. 1 shows in section, on the left-hand side, a still closed reservoir 3 (which has a receiving chamber 29 with an insert 28 which has not yet been radially pushed out). FIG. 2 shows, on the right side, a reservoir 3 the receiving chamber 29 of which has already been opened on the outlet side, and with the insert 28 moved radially so as to protrude from the opening 30.

The connecting device 24 in this embodiment has a connecting element 34 for creating a fluidic connection with the respective receptacle 4 for supplying the delivery medium, in particular, so that the delivery medium can be supplied, for example, through a delivery channel 35 as shown by the delivery device 5 via the connecting element 32 of the respective receptacle 4—i.e., the respective insert 28 or its storage chamber 31—for delivery, and in particular, for atomization of the respective dose of formulation.

The fluidic connection is preferably also created by the axial movement of the reservoir 3 relative to the housing 13 or connecting element 34. In particular, the finger 33 first engages axially in the respective receiving chamber 29 in order to move the insert 28 which is to be used next in the radial direction. After this radial movement, as the axial movement continues, the connecting element 34 engages in the receiving chamber 29 and in the insert 28. For this purpose, the connecting element 34 is constructed, in particular, as a piercing element, for example, in the form of a cannula or needle with a corresponding point, so as to assist in particular, with the piercing or other penetration of the storage chamber 31 in order to create the desired fluidic connection. Thus, the fluidic connection for the delivery medium to the storage chamber 31 is provided and the delivery medium can be supplied to the storage chamber 31 for the expulsion of the formulation 2.

In the embodiment shown, the outer engagement member 25, the finger 33 and the connecting element 34 form the connecting device 24 or components thereof. However, other constructional solutions are possible for opening or piercing the receptacles 4 one after another or as necessary on the supply side and/or on the outlet side and/or for connecting them to the delivery device 5 or for creating another fluidic connection, e.g., for the direct supply or intake of ambient air, and in particular, for moving the relevant insert 28 preferably radially, but optionally also axially, for opening the respective openings 30 of the receiving chamber 29 and/or for connecting the storage chamber 31 in the insert 28 to the supply of delivery medium, in particular, for inserting the connecting element 34 into the storage chamber 31.

In the embodiment shown, in particular, an axial movement leads to the opening, connecting or piercing through the connecting device connecting device 24, preferably at right angles to the direction of delivery 11 or the direction of conveying of the receptacles 4 or the direction of movement or rotation of the reservoir 3. In particular, axial connection or piercing is carried out in the embodiment shown. However, radial or other connection or piercing is also fundamentally possible, and this can also be effected, if necessary, by means of the axial movement provided or carried out by the gear 15. Theoretically, the direction of connection, opening, piercing and/or delivery 11 may run radially.

Particularly preferably, the connecting device 24—in particular, like the delivery device 5 and/or transporting device 23—may be actuated by opening and/or closing the cover 10 and/or may be actuated by the preferably common gear 15 or at least one axial movement.

According to another feature explained hereinafter with reference to an alternative embodiment, it is also possible to arrange the transporting device 23 and/or the connecting device 24 inside the annular arrangement of the reservoir 3 or receptacles 4. This, in turn, contributes to a particularly compact structure for the atomizer 1, and in particular, helps to minimize the axial height of the atomizer 1.

The reservoir 3 is preferably rigid. The term "rigid" is to be taken to mean that the reservoir 3 or its receiving chambers 29 preferably form a sufficiently stable or well-defined holder and possibly guide for the inserts 28. However, other constructional solutions are possible. For example, by externally guiding the reservoir 3 or the respective receiving chamber 29, it is possible to achieve the desired guiding of the insert 28 contained in the receiving chamber 29, even if the reservoir 3 is not of rigid construction, for example. Alternatively or additionally, the insert 28 may be removed completely from the reservoir 3 for connecting the receptacle 4 or when opening the receiving chamber 29 or for delivering the respective dose. In this case, in particular, the reservoir 3 may also be, for example, constructed only as a blister pack or other package.

FIG. 2 shows the atomizer 1 in the activated state. Ambient air is sucked into the pump chamber 6. The spring 14 is tensioned. The receptacle 4 selected for delivering the next dose has been opened and connected, the corresponding insert 28 has been pushed radially outwards and connected to the supply of delivery medium by means of the connecting element 34, in particular, pierced by the latter.

In the embodiment shown, the actual delivery, and in particular, the atomization of the formulation 2 or dose contained in the pierced receiving chamber 29 can only take place after a corresponding triggering or further actuation, for example, after another or further actuation of the cover 10 but, in particular, as a result of the actuating element 21, which has preferably only moved axially outwards in this state, being actuated, particularly pressed axially inwards by a user or patient. This releases the latch or other engagement means, so that the spring store or the spring 14 can relax. The delivery medium in the pump chamber 6 is put under pressure and conveyed through the delivery channel 35 and the connecting element 34 into the adjoining storage chamber 31. The delivery medium continues to flow through the channel 32 and out of the insert 28, the formulation 2 contained in the storage chamber 31 being expelled at the same time. The resulting aerosol or spray cloud is emitted through the optional grid 9 through the mouthpiece 8, so that the user or patient can inhale the formulation 2 which has been emitted and in particular, atomized.

FIG. 5 shows a schematic section of the atomizer 1 after inhalation, i.e., with the spring 14 relaxed, the receptacle 4 empty and the cover 10 still open.

After the inhalation or after the delivery of the formulation 2, the cover 10 is closed again. This is done, in particular, in the opposite direction of rotation. Because of the coupling provided—in particular, by means of the gear 15—the inner engagement member 19 is moved back again in the axial direction into its starting position shown in FIG. 1, while the spring store or the spring 14 is tensioned again and finally the operative connection or other axial connection between the engagement member 19 and the delivery device 5 or the spring store—particularly via the locking arm 20—is re-established, so that the starting position shown in FIG. 1 with the spring 14 relaxed and with the desired retaining connection between the engagement member 19, and particularly the bellows 7 and/or the spring 14, is recreated. Moreover, the reservoir 3 is moved back into its axial starting position, i.e., pushed axially back in the opposite direction. In particular, this releases the reservoir 3 from the finger 33 and from the connecting element 34.

The advancing or further rotation of the reservoir 3 by one receptacle is preferably superimposed on the axial movement, and this always takes place during the up and down movement, i.e., during the opening and/or closing of the cover 10, when the connecting device 24—particularly the fingers 33 and connecting element 34 thereof—is no longer engaging in the reservoir 3 but is allowing the desired rotary movement. Therefore, in the embodiment shown, the sliding guide or control cam 26 is preferably designed so that the desired advance or further rotation of the reservoir 3 by one receptacle 4 takes place during only part of the axial movement.

The measures described above result in a very compact, simple structure of the atomizer 1, particularly with few components.

The proposed atomizer 1 can be operated very simply and intuitively. Essentially, all that is needed to operate it is to open and close the cover 10. All the functions or processes envisaged are triggered or controlled thereby or take place automatically. In addition to actuation of the cover 10, when the atomizer 1 is constructed as an active atomizer 1, it only remains to trigger the actual delivery and atomization after opening the cover 10. This is preferably done by actuating, particularly pressing, the actuating element 21. As the actuating element 21 is preferably only actuatable, axially moved out and/or accessible once the atomizer 1 has been activated, i.e., once the cover 10 has been opened, simple intuitive operation is made possible and incorrect operation is ruled out.

The actuating element 21 passes, in particular, through an opening in the cover 10. However, here again, different embodiments are possible. In addition, it is also possible for the actuating element 21 to be accessible, e.g., revealed by the cover 10, in the activated state of the atomizer 1.

After inhalation, the atomizer 1 or the cover 10 can be closed again. Preferably, the cover 10 is secured against closure as long as the actuating element 21 has not been actuated, i.e., in the embodiment shown, is still in the axially extended position, or until the formulation 2 has been delivered from the receptacle 4, which has already been opened or connected up or pierced.

Figure 3:
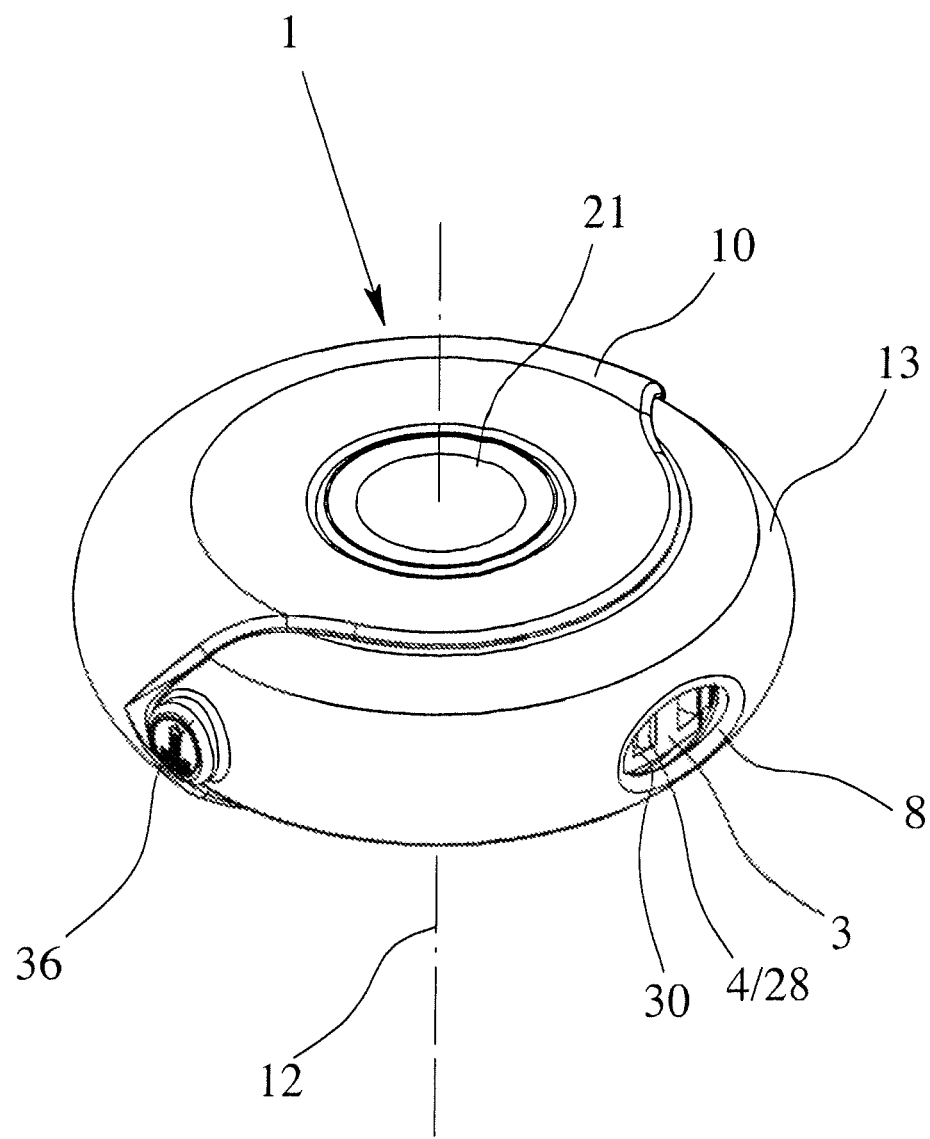
FIG. 3 is a perspective view of the atomizer in the opened or activated state.

FIG. 3 shows the proposed atomizer 1 in the opened or activated state. The cover is thus rotated by about 160° to 180° relative to the closed transportation position shown in FIG. 1. The cover 10 can preferably only be rotated in opposite directions to open and close it. Preferably therefore a rotation stop 36 is provided which is visible from the outside in the embodiment shown and protrudes for example, from the periphery or housing 13. This helps to ensure simple and intuitive operation of the atomizer 1, as the user intuitively grasps how far and in which direction the cover 10 has to be opened or closed. Particularly preferably, the atomizer 1 is constructed so that the rotation stop 36 forms a stop both for the cover 10 in the open state and also for the cover 10 in the closed state. Alternatively, separate projections or stops could also be provided for this purpose.

Figure 4C:
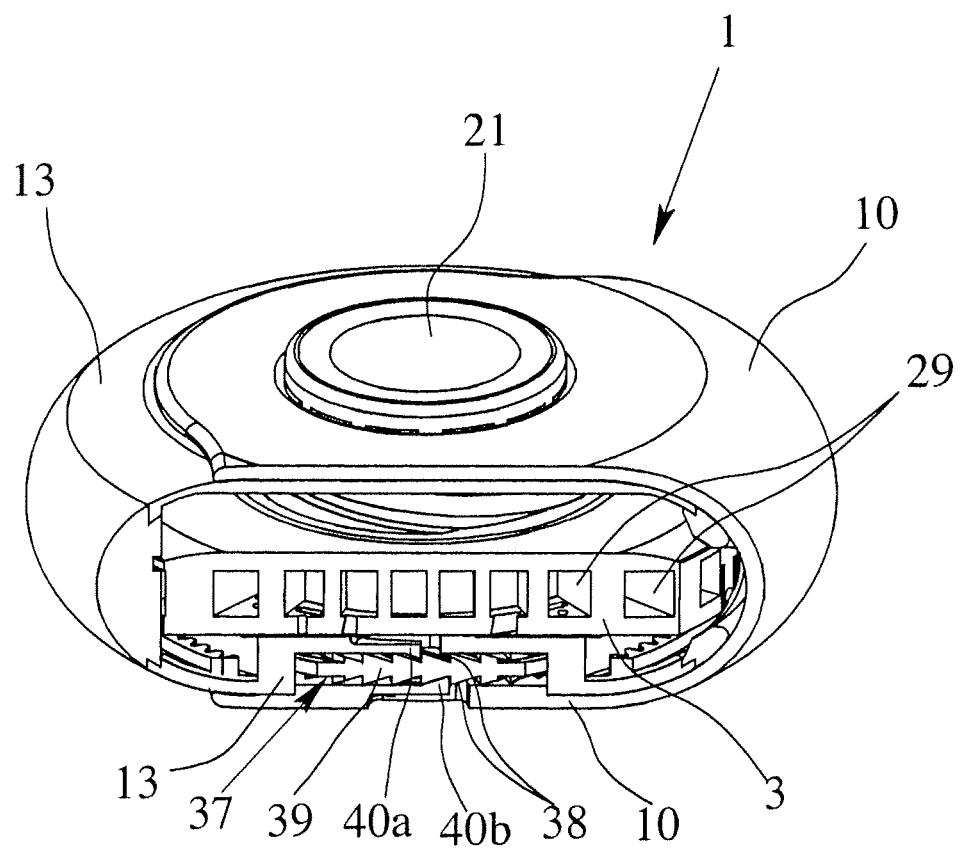
FIG. 4c is a schematic cross section of the atomizer according to FIG. 1 with a locking device.

The atomizer 1 or cover 10 also preferably comprises a locking device 37 shown in FIG. 4c (partial cross section of the atomizer 1 in the activated state) which ensures that the cover 10 can only ever be opened and closed alternately. For this purpose, at least one corresponding latch 38 or the like is provided, for example, between regions of the cover 10 and housing 13 arranged axially above or behind one another, providing the desired functionality.

Figure 4D:
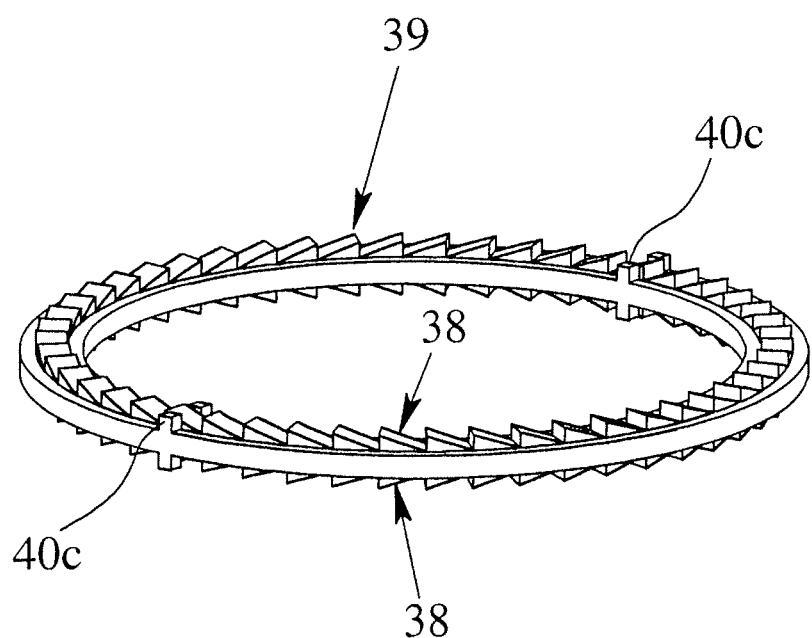
FIG. 4d is a perspective view of a control ring of the locking device according to FIG. 4c.

Preferably, the atomizer 1 or the locking device 37 comprises a control ring 39 which is shown separately in perspective view in FIG. 4d. The control ring 39 is provided with teeth or a latch 38 on both of its axial or flat sides. The control ring 39 is rotatably guided, in particular, in an annular channel or the like in the atomizer 1 or the housing 37 thereof, as shown in FIGS. 1, 2 and 4c.

Engaging in a latch 38 of the control ring 39 is a locking arm 40a on the housing side while engaging in the other latch 38 is a locking arm 40b on the cover side, as indicated in FIG. 4c. The latches 38 and locking arms 40a, 40b are matched to one another such that the cover 10 is initially only movable or rotatable in one direction relative to the housing 13, and hence rotation in the opposite direction is prevented by the locking device 37 or by locking arms 40a or 40b acting in the opposite direction.

Preferably, a plurality of locking arms 40a are provided on the housing 13, which engage in the associated latch 38 of the control ring 39 and allow the control ring 39 to rotate only in one direction relative to the atomizer 1 or housing 13. Accordingly, a number of locking arms 40b are preferably also arranged on the cover 10 or associated therewith and allow the control ring 39 to rotate in only one direction of rotation relative to the cover 10.

To ensure that the cover 10 can only be fully opened or closed alternately, the rotation of the control ring 39 relative to the housing 13 or to the cover 10, which is in any case only possible in one direction, can alternately be blocked off and only re-activated or unlocked when the respective end position is reached, i.e., either in the fully opened or fully closed position. This locking of the control ring 39 relative to the housing 13 or to the cover 10 will be explained briefly hereinafter with reference to another cross section of the atomizer 1 according to FIG. 4e.

Figure 4E:
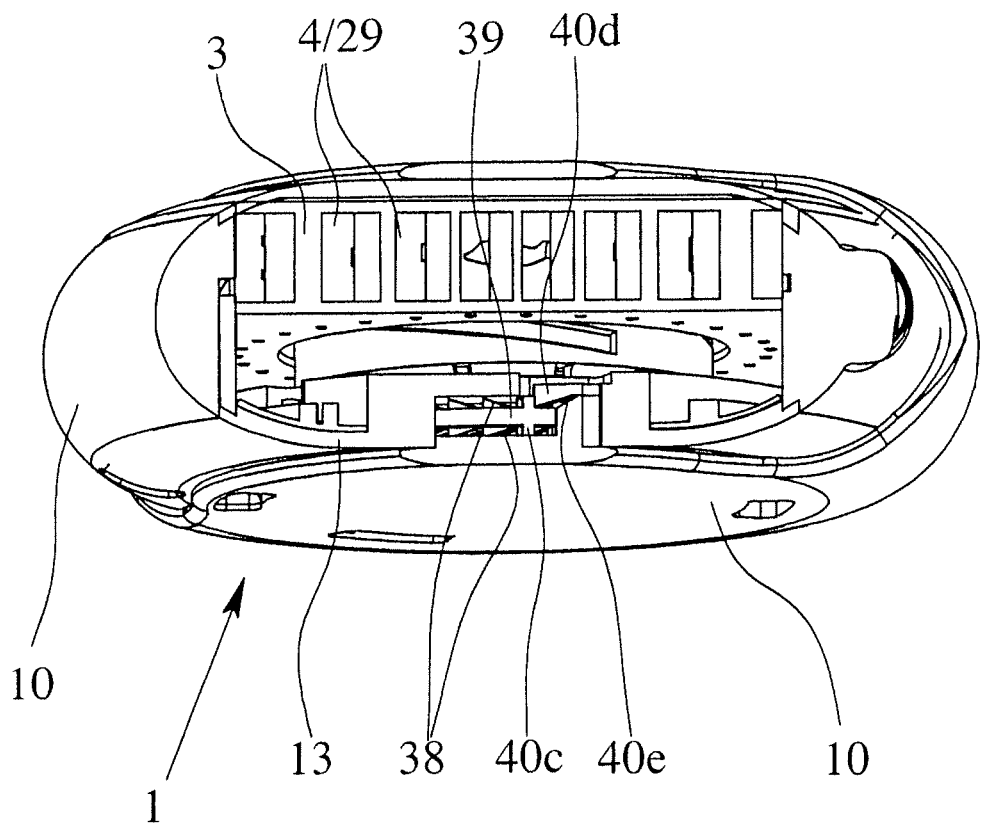
FIG. 4e is another schematic cross section of the atomizer with the locking device according to FIG. 4c.
Figure 5:
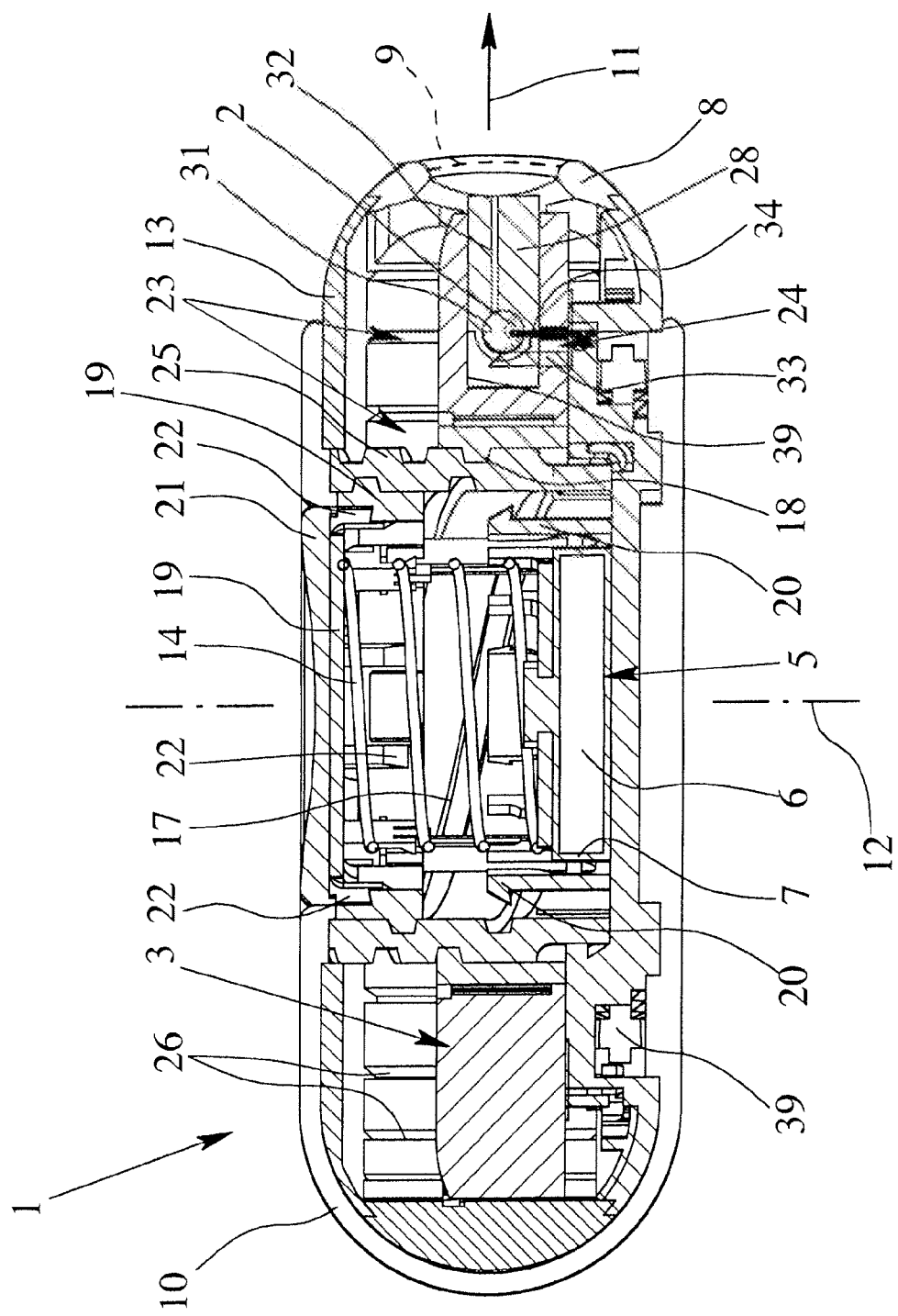
FIG. 5 is a schematic cross section of the atomizer according to FIG. 1 after a delivery or atomization.

On the control ring 39 are formed stops 40c, as shown in FIG. 4d, which cooperate with stop arms 40d as shown in FIG. 4e. FIG. 4e shows, by way of example, the locking of the control ring 39 against rotation relative to the housing 13. This locking is carried out in a corresponding or similar manner between the cover 10 and the control ring 39 and acts during the opposite movement of the cover 10 relative to the housing 13.

In the above-mentioned locking, at least one stop 40c strikes against at least one stop arm 40d, so that the rotation of the control ring 39 relative to the housing 13 which would otherwise be possible in the direction of rotation which is not blocked off by the locking arm 40a and its associated latch 38 is also blocked. This blocking by the stop arm 40d remains until the cover 10 moves into its end position.

When the end position is reached, a control slope or sliding surface 40e formed on the cover 10 leads to a springing of the stop arm 40d, so that now the previously blocked stop 40c is freed and hence the cover 10 can be turned back relative to the control ring 39 and also rotated or moved in the opposite direction. At the same time, in this end position, another stop 40c of the control ring 39 (not shown in FIG. 4e), comes to abut on a stop arm 40d arranged on the cover 10, thereby blocking the relative rotatability of the control ring 39 relative to the cover 10. As a result, the cover 10 can now only be rotated or moved together with the control ring 39 in the opposite direction until the other end position is reached. In the other end position, again, the rotation of the control ring 39 relative to the housing 13 is blocked accordingly, and in turn, the rotatability of the cover 10 is freed relative to the control ring 39. Accordingly, the cover 10 can only be fully opened or closed alternately, so as to ensure simple and intuitive operation or actuation and in particular, to rule out incorrect operation.

The embodiment shown illustrates an active atomizer 1. Theoretically, however, the atomizer 1 may also be constructed as a passive atomizer. In this case, the delivery device 5 and/or the energy store or spring store can be dispensed with. Instead, for example, ambient air can be taken in by the action of breathing during inhalation, and this air is conveyed through the respective receptacle 4—particularly, the receiving chamber 29 and the channel openings 30 of the insert 28 in question—to the mouthpiece 8, so that the formulation 2 is delivered or expelled and atomized in the desired manner.

If required the spring store may also be used independently of the delivery device 5, for example, for advancing and/or opening or closing the receptacles 4, particularly for driving and/or actuating the transporting device 23 and/or the conveying device 24.

If the atomizer 1 does not have a delivery device 5 and/or an energy store, the actuating element 21 and an actuation required in addition to the movement of the cover 10—i.e., an additional triggering of the actual release and atomization of the formulation 2—may be omitted. Rather, it is then preferably sufficient to open the cover 10 in order to activate the atomizer 1, so that the next receptacle 4 is ready directly with its dose or formulation 2 for inhalation and inhalation can take place immediately.

The mouthpiece 8 is preferably of fixed construction and/or radially aligned and/or preferably formed directly on the housing 13. This results in a simple and compact structure of the atomizer 1 with, in particular, an at least substantially smooth outer contour. However, the mouthpiece 8 may also theoretically be movable, e.g., foldable, slidable, telescopically extendable or movable in some other way. Alternatively or additionally, the mouthpiece 8 may also be aligned or arranged in a different direction, e.g., diagonally or axially, for delivering the formulation 2 or the aerosol.

The proposed atomizer 1 preferably additionally comprises a counter (not shown).

The proposed atomizer 1 preferably operates purely mechanically.

The proposed atomizer 1 is preferably made up at least essentially of only plastics components or parts or made at least essentially only of plastics. Only the spring 14 and optionally the grid 13 may be made of metal, if necessary.

According to a further feature, the manual actuation of the active delivery and atomization of the formulation 2, which is carried out in the first embodiment by pressing the actuating element 21, in particular, may also be omitted. Instead, an actuation controlled by breathing in is preferably provided. For example, when a corresponding vacuum is produced in the atomizer 1 by breathing in, the holding connection between the inner engagement member 19, on the one hand, and the biased spring 14 or the bellows 7, another conveying or pumping element or the like, on the other hand, can be undone in order to enable the desired delivery, and particularly, the atomization of the formulation 2 to take place virtually automatically during inhalation, namely by means of the energy stored in the energy store or spring store.

Some additional embodiments of the proposed atomizer 1 will be described in the following, with only the essential differences or new aspects compared with the first embodiment being emphasized. The explanations and remarks given hereinbefore therefore preferably still apply as they stand or in supplementary or similar fashion.

Figure 6:
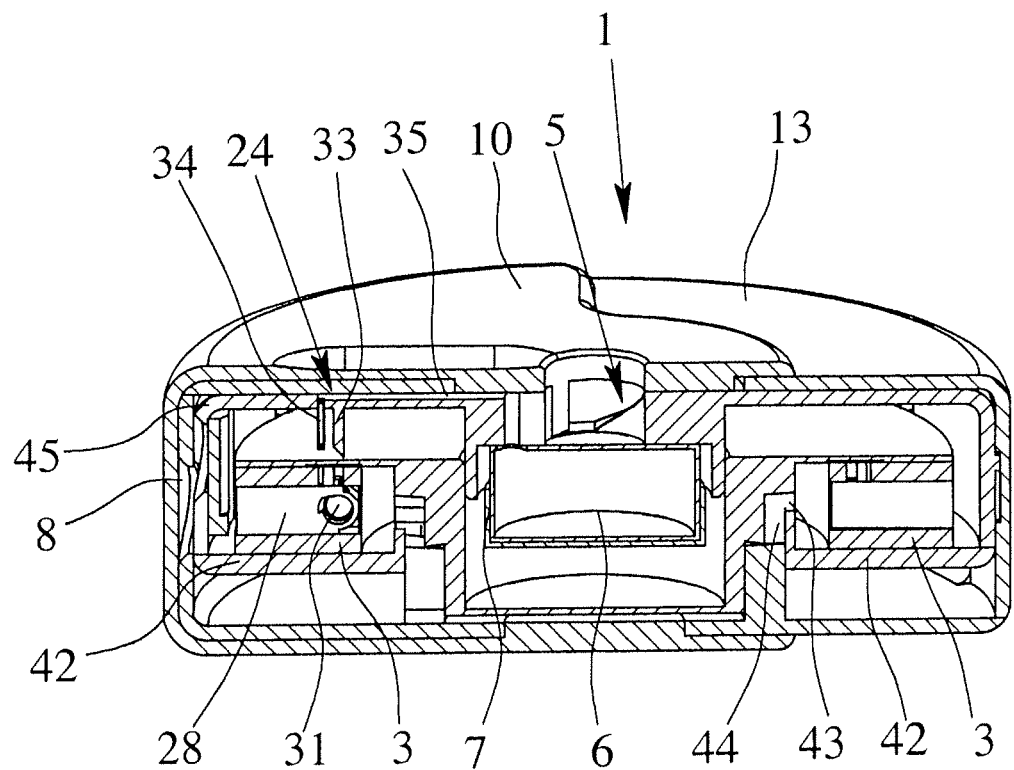
FIG. 6 is a schematic cross section of an atomizer according to a second embodiment in the transportation position.
Figure 7:
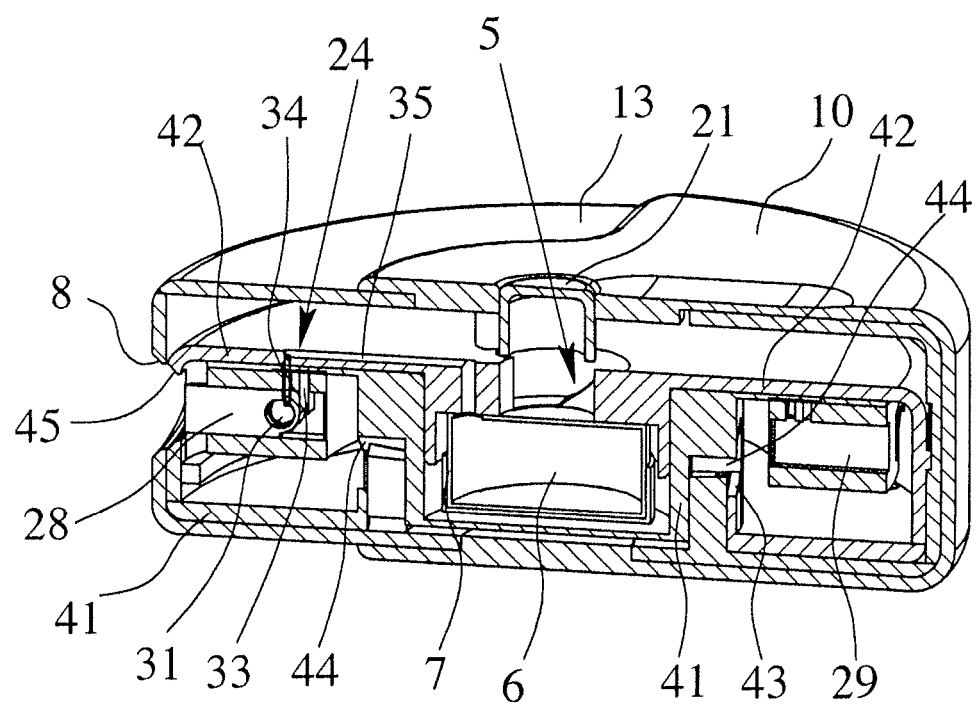
FIG. 7 is a schematic cross section of the atomizer according to FIG. 6 in the activated or opened state.

FIGS. 6 & 7 show schematic views of a second embodiment of the proposed atomizer 1. FIG. 6 shows the atomizer 1 in the closed position with the receptacle 4 not yet pierced. FIG. 7 shows the atomizer 1 in the activated state with the receptacle 4 opened or pierced.

In the second embodiment, the reservoir 3 is not axially movable, in contrast to the first embodiment. Instead, the connecting device 24 is preferably axially slidable or movable. In the embodiment shown, the reservoir 3 is held by a rotatable inner part 41. The connecting device 24 (at least the connecting element 34 thereof and preferably the fingers 33 thereof) is mounted on a carrier 42, which is axially movable but not rotatable. The carrier 42 is, in turn, preferably axially movable by opening and/or closing the cover 10, particularly by means of the gear 15 which is not shown in detail here.

The carrier 42 preferably has axially operating teeth 43, e.g., with sawtooth-shaped sliding surfaces or the like, which cooperate with complementary or corresponding mating teeth 44 provided or formed on the inner part 41, and in particular, engage therein such that the axial movement of the carrier 42 causes a defined, stepwise further rotation of the inner part 41 with the reservoir 3.

In a second embodiment, the carrier 42 fits over or around the inner part with the reservoir 3 preferably peripherally, and in particular, in such a manner that the carrier 42 extends from an end face of the inner part 41 around the outside of the reservoir 43 to the other end face of the reservoir 3 and radially back inwards to an inner edge on which the preferably axial teeth 43 are formed. The carrier 42 has a peripheral opening 45 which, at least in the activated state, lies on an extension of the particular receptacle 4 which has been opened or pierced, or of the radially advanced insert 28, such that the delivery of the formulation 2 is made possible and not obstructed.

In the second embodiment the same operating procedure is used as in the first embodiment.

Figure 8:
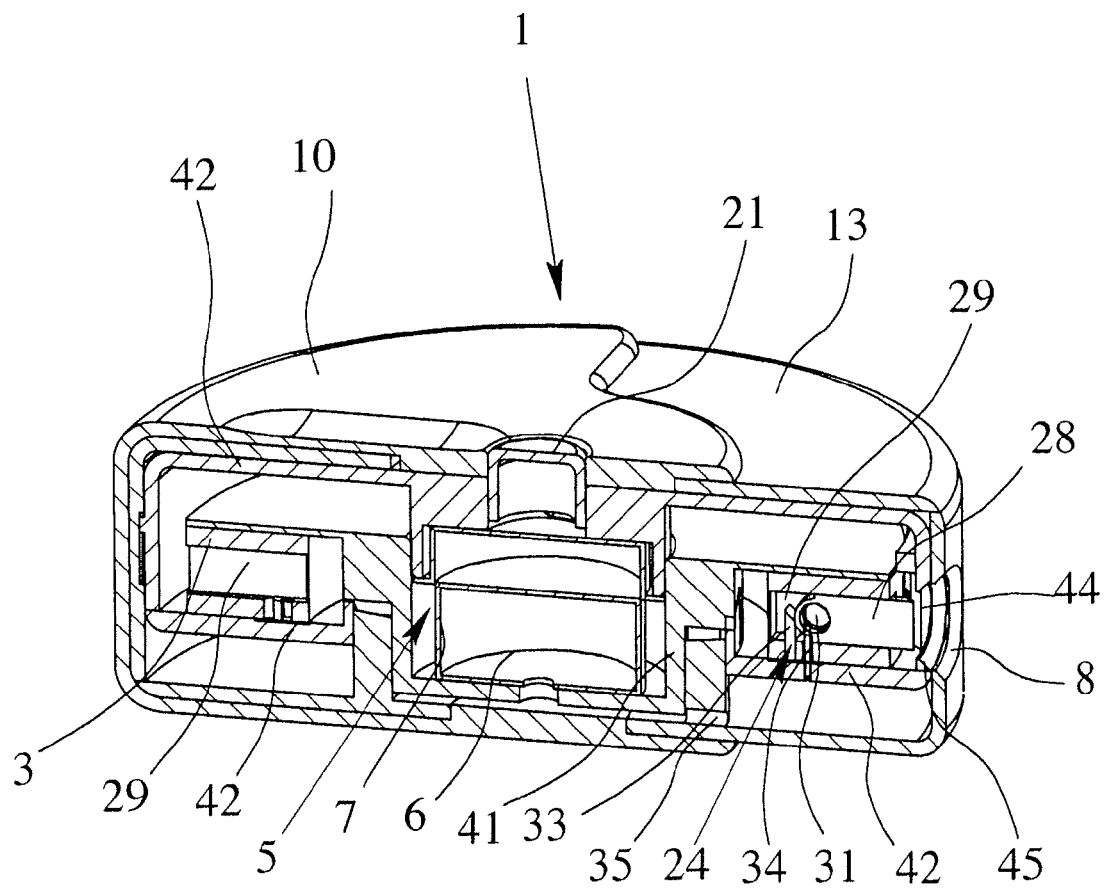
FIG. 8 is a schematic cross section of an atomizer according to a third embodiment in the opened or activated state.

FIG. 8 shows a schematic sectional view of a third embodiment of the proposed atomizer 1 in the opened, activated state. The third embodiment largely corresponds to the second embodiment, although the connecting device 24 does not engage, as in the second embodiment, from the flat side covered by an annular flange of the inner part 41, but from the opposite flat side into the reservoir 3—particularly with the finger 33 and the connecting element 34.

Figure 9:
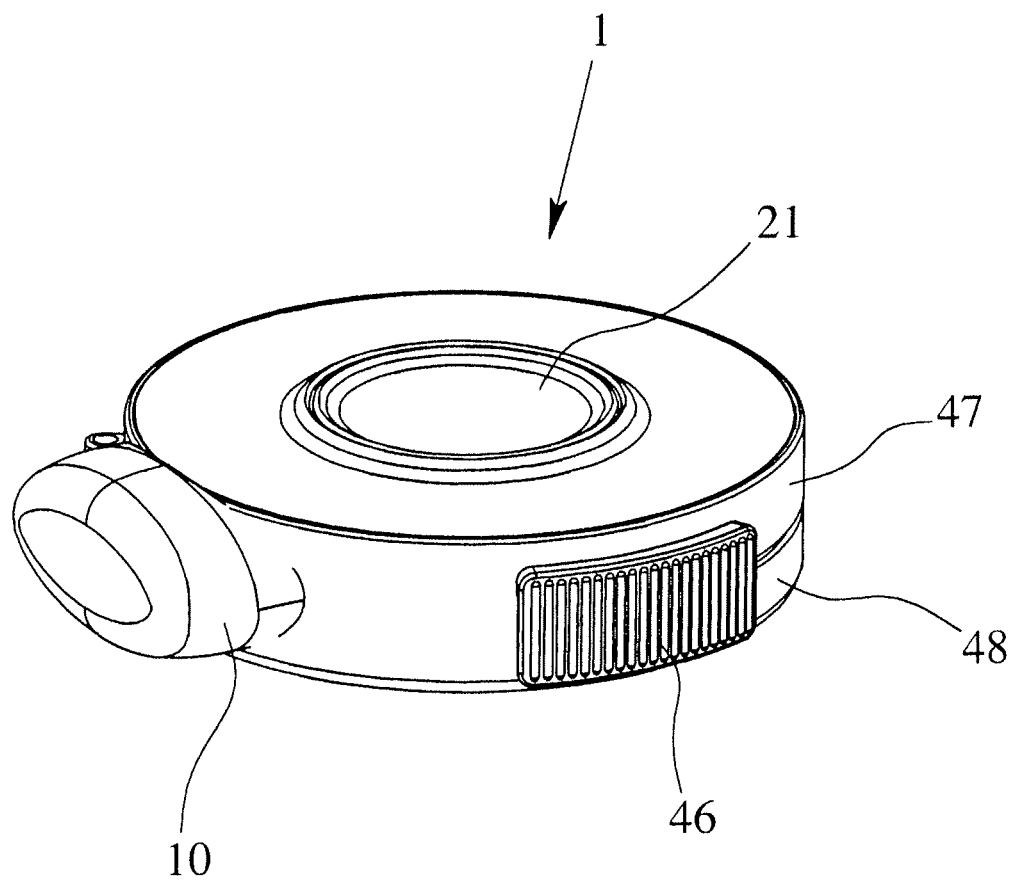
FIG. 9 is a schematic view of an atomizer according to a fourth embodiment in the transportation position.

FIG. 9 shows in schematic view a fourth embodiment of the proposed atomizer 1 in the transportation position or locked state. Here, the cover 10 is in the form of a cap. The pivot axis of the cover 10 is eccentrically arranged or formed, particularly in the region of the periphery or edge of the atomizer 1. In contrast to the previous embodiments, the cover 10 essentially only covers the mouthpiece 8.

In the fourth embodiment, the opening and/or closing of the cover 10 is preferably not coupled with the other functions of the atomizer 1.

The atomizer 1 has a release mechanism 46 which is constructed, in particular, as a peripherally movable slide.

Figure 10:
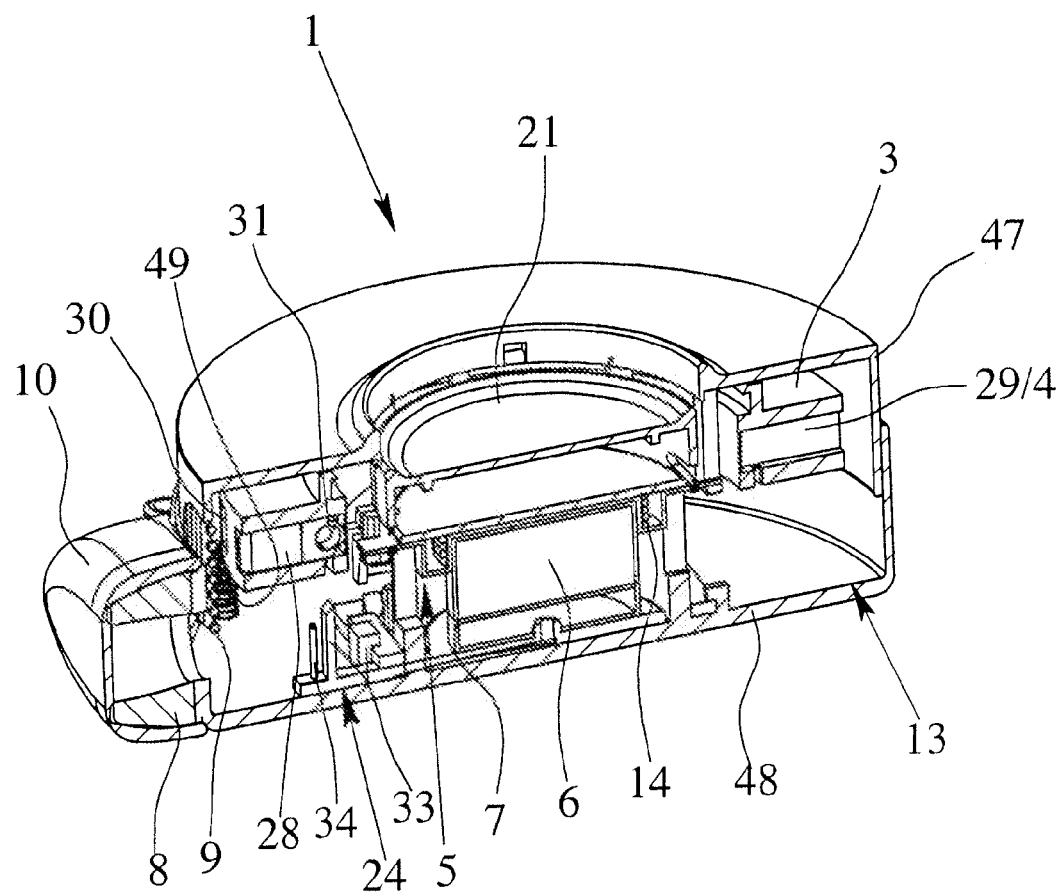
FIG. 10 is a schematic cross section of the atomizer according to FIG. 9 in the unlatched state.

FIG. 10 is a schematic sectional view the atomizer 1 in the unlocked state.

In the fourth embodiment, the atomizer 1 has two preferably external housing parts, particularly an upper housing part 47 and a lower housing part 48, which are movable axially towards one another. In particular, the housing parts 47, 48 are biased away from one another preferably by a plurality of spring elements 49 so that, in the unlocked and non-compressed state, the upper housing part 47 is axially raised relative to the lower housing part 48, as shown in FIG. 10.

The two housing parts 47, 48 are movable axially together counter to the force of the spring elements 49. In the axially compressed state, the two housing parts 47, 48 are latchable together, in particular. This latching can be released by actuating the release mechanism 46.

Starting from the transportation position, after release, the upper housing part 47 is automatically moved axially away from the lower housing part 48 by the spring elements 49. This movement away or lifting movement causes actuation of the delivery device 5, namely enlargement of the pump chamber 6 and an intake of ambient air. Moreover, the spring 14 associated with the delivery device 5, particularly its bellows 7, is axially tensioned or compressed thereby. The spring elements 21 accordingly have a greater spring force than the spring 14.

Moreover, the above-mentioned axial or lifting movement causes the actuating element 41 associated with the spring 14 to be raised axially or moved out.

Furthermore, the axial lifting movement causes the reservoir 3 to be axially moved and separated from the connecting device 24 (not shown in detail).

Next, the two housing parts 47, 48 have to be manually pushed together axially counter to the force of the spring elements 49 by a user. During this axial movement and/or during the preceding lifting movement, the reservoir 3 is further rotated by one receptacle 4. The further rotation or advancing of the reservoir 3 is preferably carried out in turn by slidable controlling of the transporting device 23 or the like. As the process continues, the receptacle 4 that has been rotated into the delivery position is then opened and connected to the conveying device, preferably in turn through the connecting device 24 (not shown here).

Figure 11:
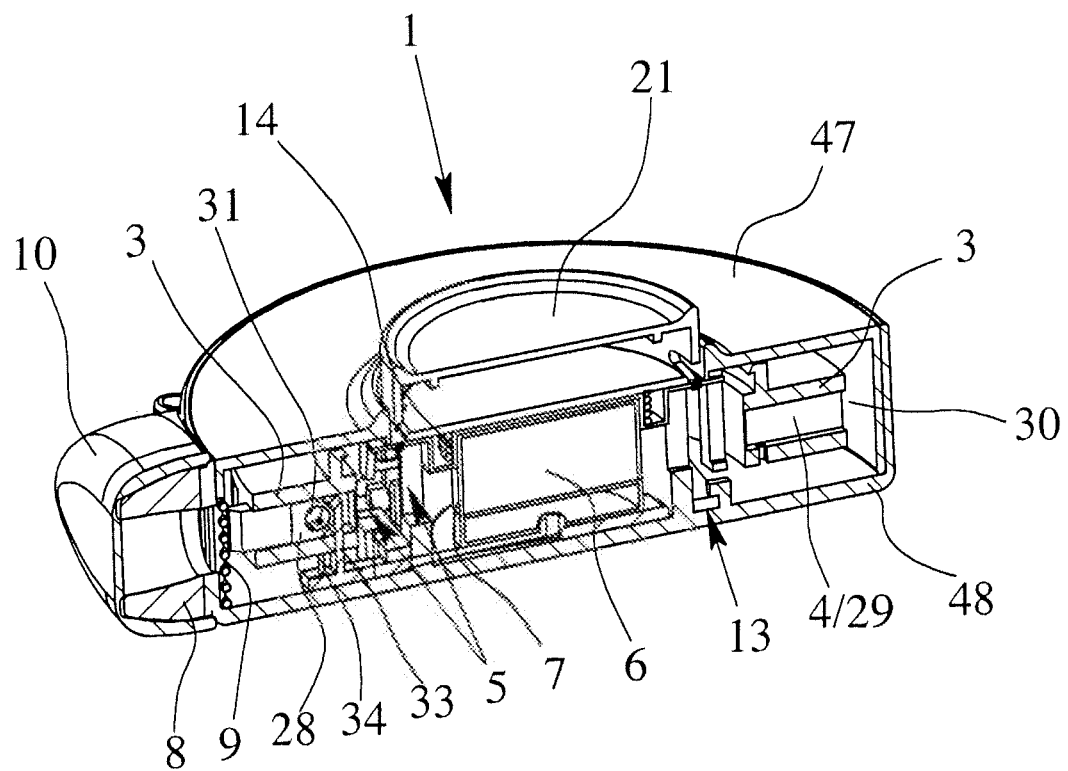
FIG. 11 is a schematic cross section of the atomizer according to FIG. 9 in the activated, pressed-together state.

FIG. 11 shows the activated state of the atomizer 1 that results after the pushing together, with the housing parts 47, 48 latched or locked together, and with the axially protruding actuating element 21. Preferably, it is only when this state is reached that it is possible to actuate the actuating element 21 or only after the cover 10 has been opened, to allow the delivery and atomization of the formulation of the dose from the opened receptacle 4.

By actuating—particularly axially pressing in—the actuating element 21, the blocking of the spring 14 is released, so that the spring 14 can relax axially and thereby actuate the delivery device 5, particularly pressurize the air contained in the pump chamber 6, so that this air is conveyed through the attached receptacle 4 and delivers the formulation 2 in the desired manner through the mouthpiece 8.

The fourth embodiment also allows very simple intuitive operation. Improper operation is prevented, in particular, by suitable blocking means.

Figure 12:
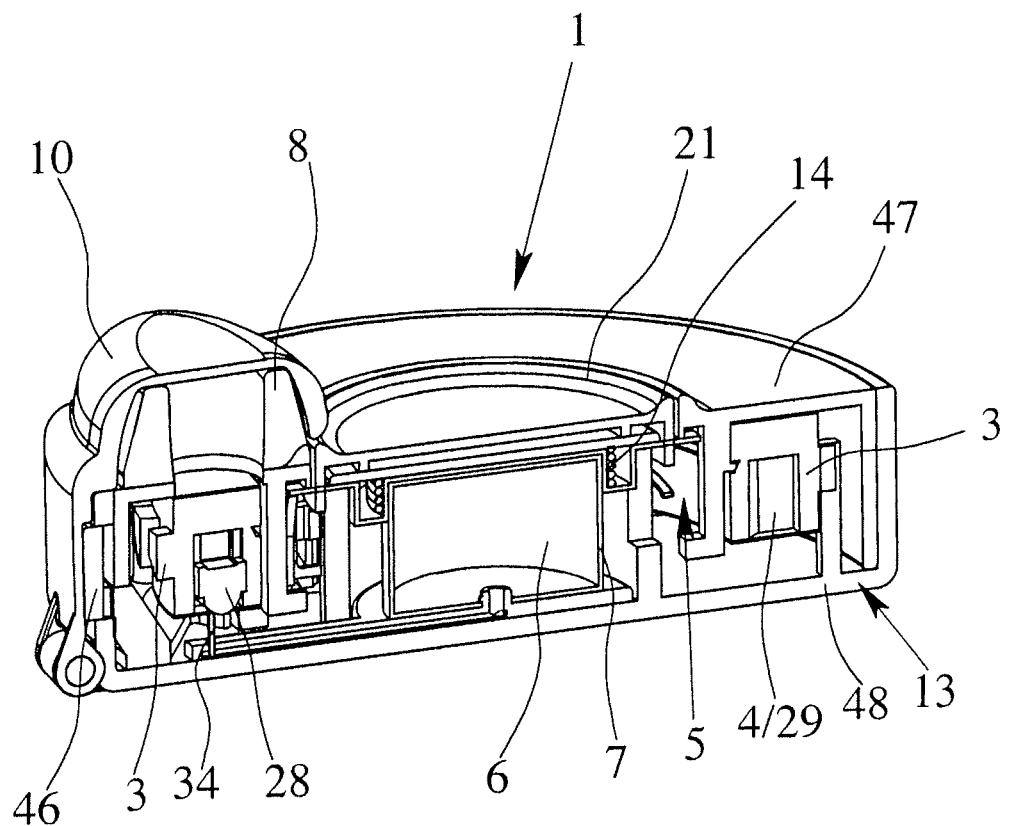
FIG. 12 is a schematic cross section of a proposed atomizer according to a fifth embodiment in the transportation position.
Figure 13:
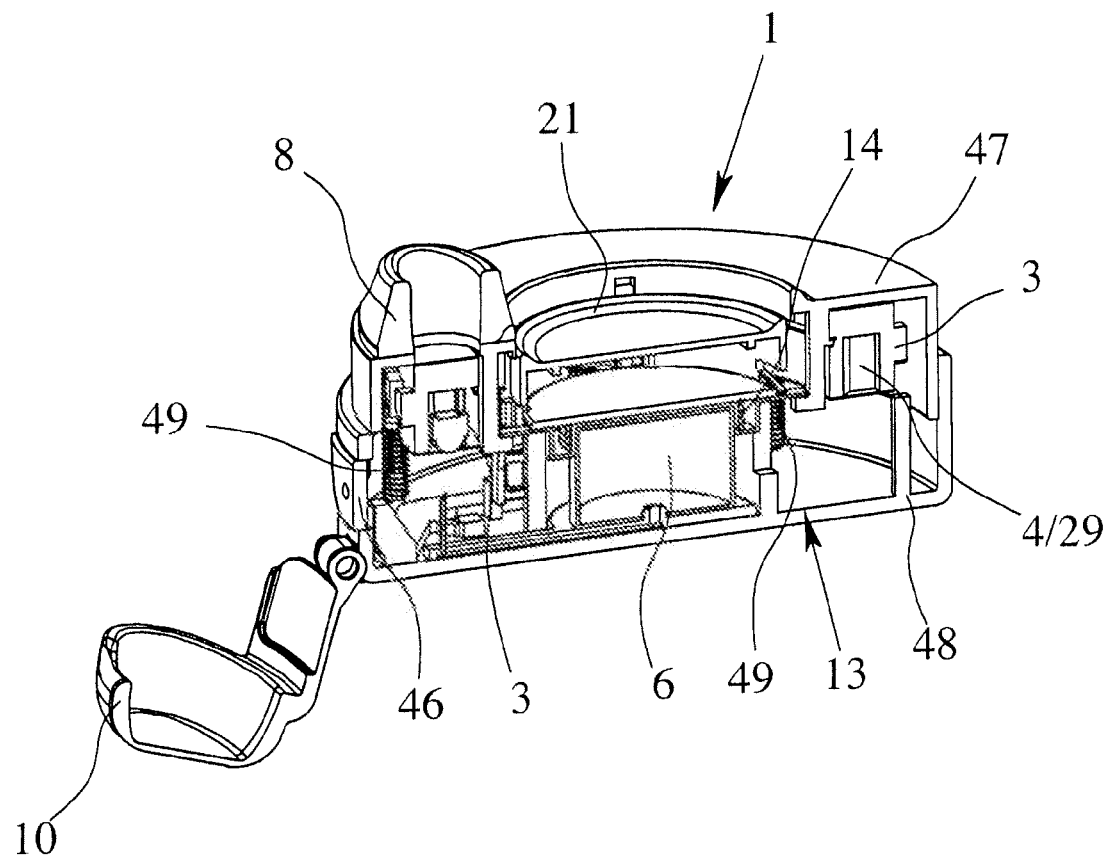
FIG. 13 is a schematic cross section of the atomizer according to FIG. 12 in the unlatched state.
Figure 14:
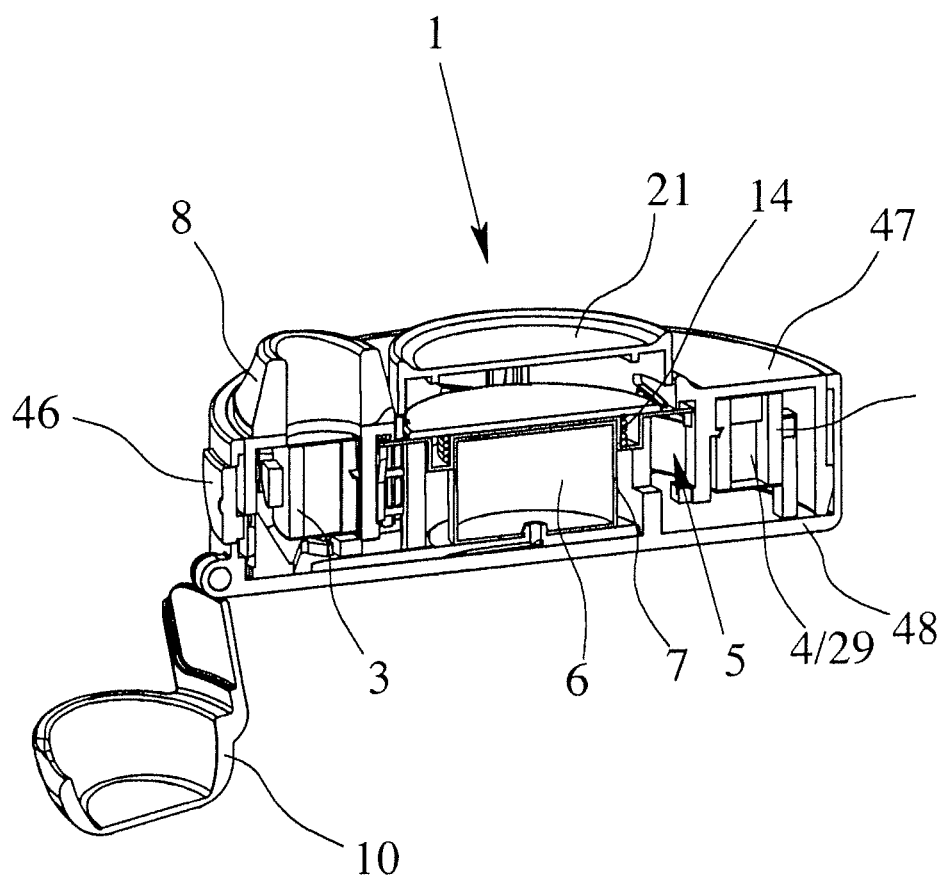
FIG. 14 is a schematic cross section of the atomizer according to FIG. 12 in the activated, pressed-together state.

FIG. 12 to 14 show a fifth embodiment of the proposed atomizer 1 in various states corresponding to those shown in FIG. 9 to 11.

The fifth embodiment differs essentially from the fourth embodiment in that the direction of opening, piercing and/or displacement and/or alignment of the receptacles 4 or inserts 28 extends at least substantially axially or parallel, but not radially relative to the axis 12 or the annular arrangement of the reservoir 3 or of the receptacles 4. In the embodiment shown, the mouthpiece 8 is accordingly arranged or formed above the reservoir 3 on the side of the atomizer 1 or housing 13—in this case, the upper housing part 47, in particular,—while the mouthpiece 8 protrudes or projects substantially at right angles or perpendicularly to the flat side of the atomizer 1.

In the fifth embodiment, starting from the transportation position shown in FIG. 12, first of all, the cover 10 has to be opened, and in the embodiment shown, it is preferably pivotable about the tangentially extending axis 12. Only when the cover 10 has been opened is the release mechanism 46 accessible. Otherwise, the procedure is the same as for the fourth embodiment.

Figure 15:
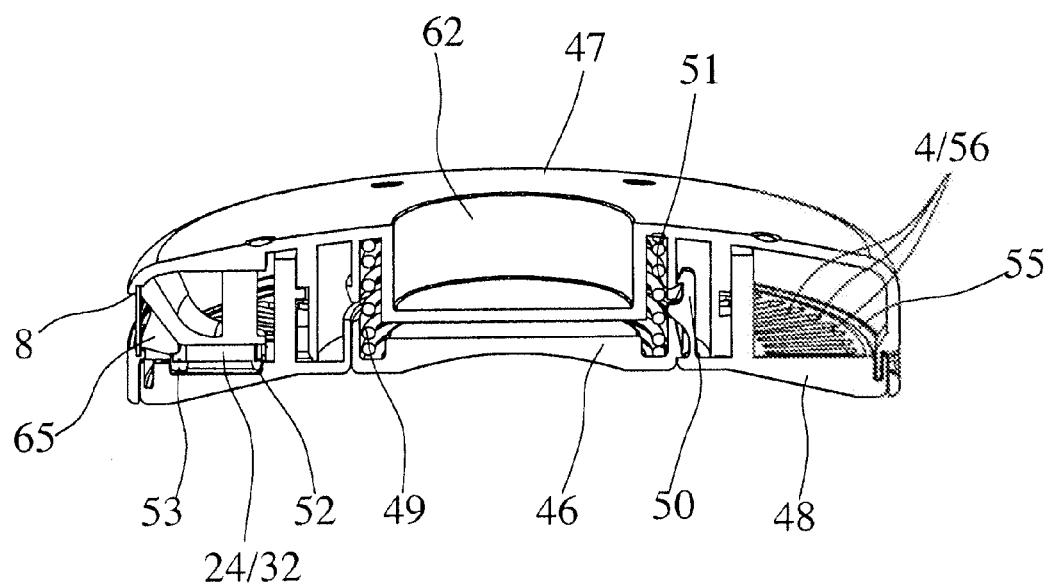
FIG. 15 is a schematic cross section of an atomizer according to a sixth embodiment in the transportation position.

FIG. 15 is in schematic sectional view of a sixth embodiment of the proposed atomizer 1 in the transportation position. The sixth embodiment resembles the fourth embodiment in particular, in principle. However, unlike the previous embodiments, the sixth embodiment does not have a delivery device 5. Rather, it is a passive atomizer 1.

In the transportation position, the two housing parts 47 and 48 which can be moved axially away from each other are latched or locked together, particularly by at least one snap-fit hook 50 or the like. The at least one snap-fit hook 50 may preferably engage behind an annular shoulder 51 or the like on the other housing part 47, 48, in order to form an interlocking holding connection between the two housing parts 47, 48 in the axial direction in the locked position.

Figure 16:
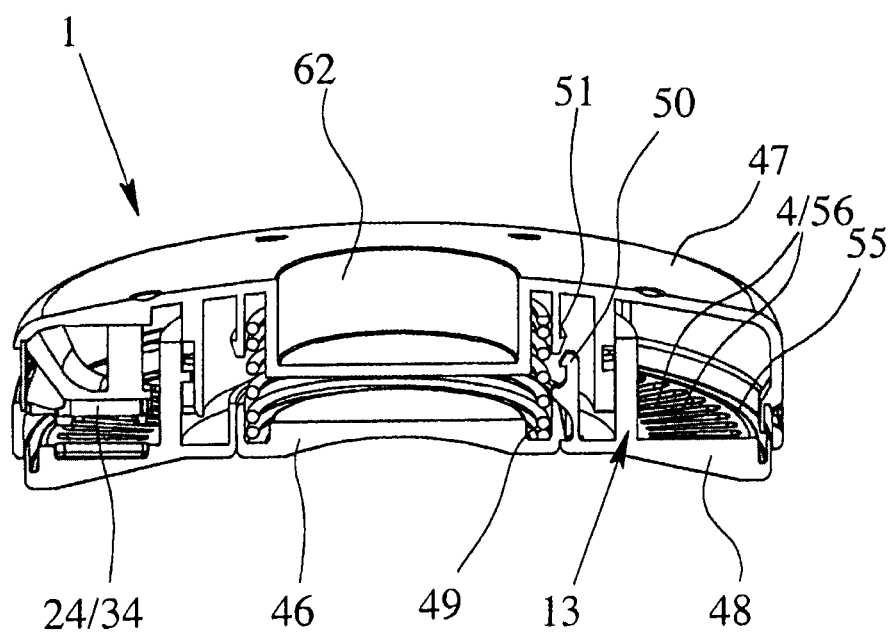
FIG. 16 is a schematic cross section of the atomizer according to FIG. 15 in the unlatched state.
Figure 17:
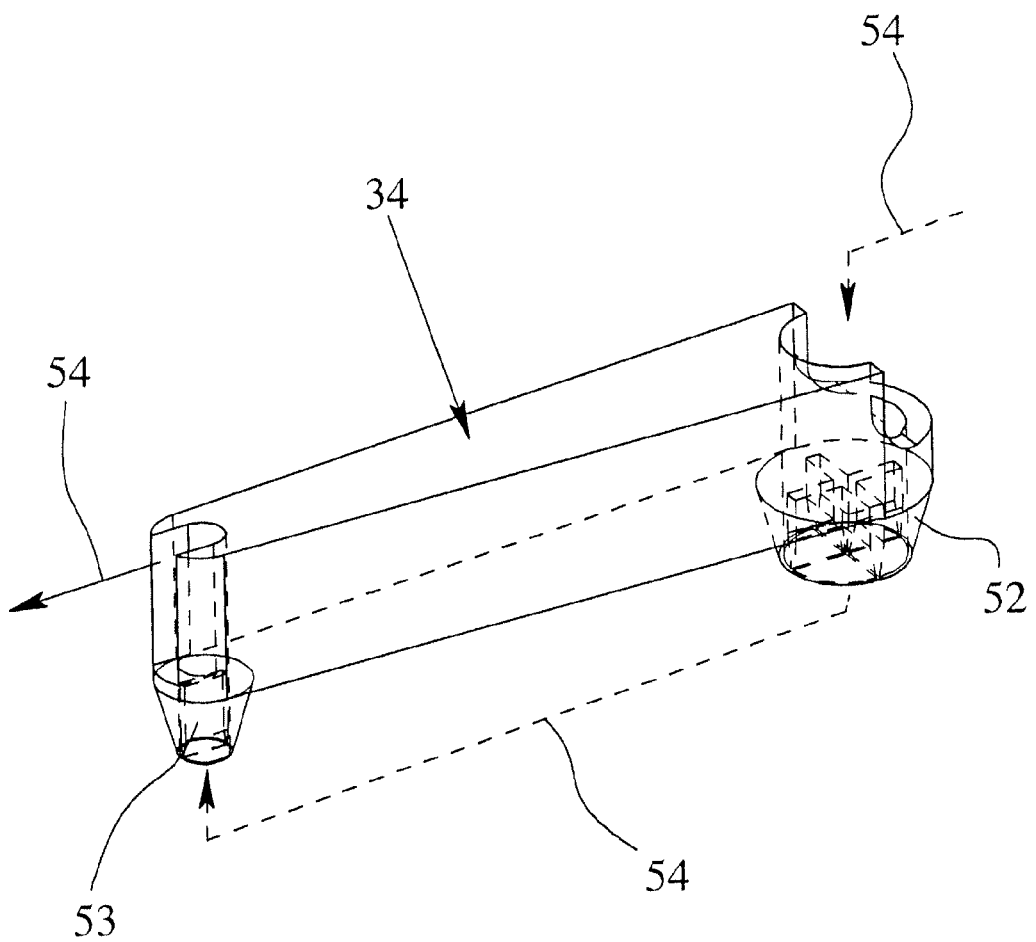
FIG. 17 is a schematic view of a connecting element of the atomizer according to FIG. 16.

In the fourth embodiment, preferably a plurality of spring elements 49 is provided. In the sixth embodiment, preferably, only a central spring element 49 is provided which is formed, in particular, by a central helical spring which braces the two housing parts 47, 48 apart. When, in this case, the central release mechanism 46 is actuated, particularly by axial pressure, the at least one snap-fit hook 50 or the like is sprung out, i.e., the latching of the two housing parts 47, 48 is undone, so that the two housing parts 47, 48 can move axially away from one another, as shown in FIG. 16. As a result of this lifting movement, the reservoir 3 is preferably rotated further by one receptacle 4. The movement away or axial movement takes place automatically as a result of the spring force of the spring element 49. This axial movement is preferably, in turn, converted by a gear or teeth, sliding guide or the like (not shown) into the desired, stepwise rotary movement of the reservoir 3. Preferably, the ballpoint pen mechanism mentioned earlier can come into play here, too. At the same time, as a result of the movement away, the connecting element 34 of the connecting device 24 can be detached from the receptacle 4 which has already been emptied during the last delivery.

Then, the two housing parts 47, 48 are pressed manually together counter to the force of the spring element 49. In this way, the spring element 49 is tensioned again and the next receptacle 4 is connected or opened by the connecting device 24, particularly, the connecting element 34 thereof. Finally, the at least one snap-fit hook 50 automatically locks the two housing parts 47, 48 together again in the pushed-together end position, as shown in FIG. 15.

Figure 18:
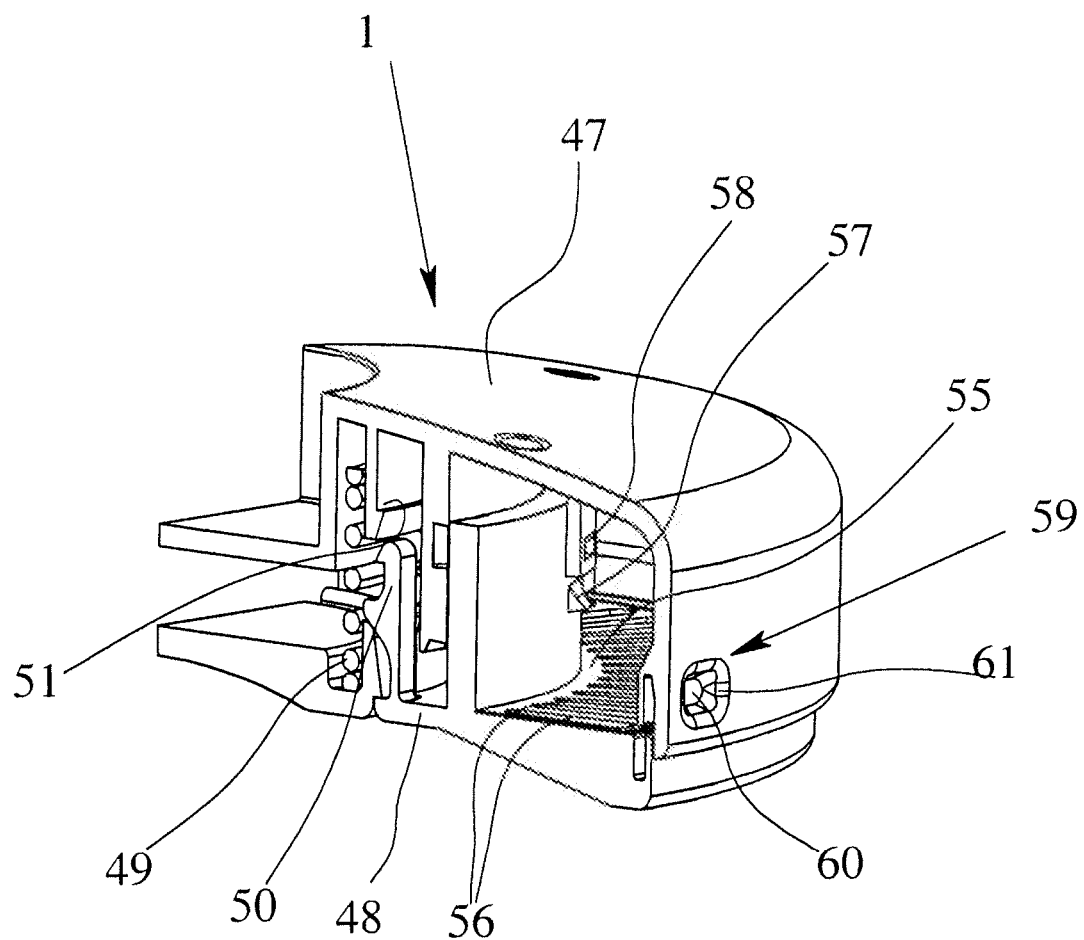
FIG. 18 is schematic view of another aspect of the atomizer according of FIG. 16.

Now, inhalation can take place. In the sixth embodiment, by breathing in, a user or patient produces an air current which is conveyed through an inlet 52 of the connecting element 34 into the opened or pierced receptacle 4 and is passed through an outlet 53 of the connecting element 34 together with the formulation 2 from the receptacle 4 to the mouthpiece 8 as schematically indicated by arrows 54 for the connecting element 34 in FIG. 17.

In the sixth embodiment, the receptacle 4 in question is preferably also axially opened or pierced. For example, the reservoir 3 is constructed here as a blister ring (not shown) comprising a plurality of blister pouches or, in particular, as an annular carrier 55 with a plurality of preferably axially open recesses 56 for receiving the blister ring (not shown) or blister pouches, as indicated in particular, in the detail shown in FIG. 18. In particular, the reservoir 3 is formed directly by the lower housing part 48 or is in particular, fixedly connected thereto, in the embodiment shown.

The sixth embodiment preferably comprises a blocking device 57 which blocks further actuation, particularly further opening of the atomizer 1 or movement of the housing parts 47 and 48 after all the receptacles 4 have been used or emptied. The blocking device 57 is, for example, formed like a hook on the reservoir 3, an associated inner part 41 or the annular carrier 55 and when the blocking position is reached, for example, engages in an abutment 58 formed on the upper housing part 47 so that the two housing parts 47, 48 can no longer be moved axially apart. This blocking is preferably irreversible as well. FIG. 18 shows the housing parts in the position where they are still apart from each other.

Figure 19:
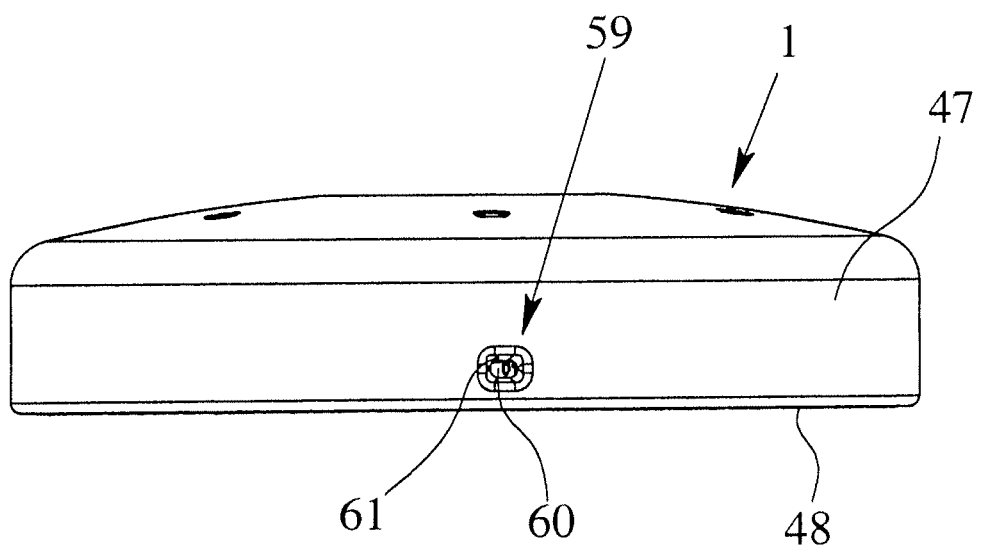
FIG. 19 is a side view showing a detail of the atomizer according to FIG. 15 with a counter in the transportation position.

The sixth embodiment, like the others, preferably comprises a counter 59 which, in the embodiment shown, preferably comprises a corresponding scale 60 on the reservoir 3, particularly on the outer periphery of the reservoir 3 or lower housing part 48, and a corresponding window 61 in the housing 13, particularly the upper housing part 47. The relative rotational position of the reservoir 3 corresponds to the number of receptacles 4 which have already been used or are still available for use. Accordingly, the scale 60 can indicate the number of receptacles 4 which are still available for use or have already been used. FIG. 19 shows the counter 59 in a cut-away side view.

Figure 20:
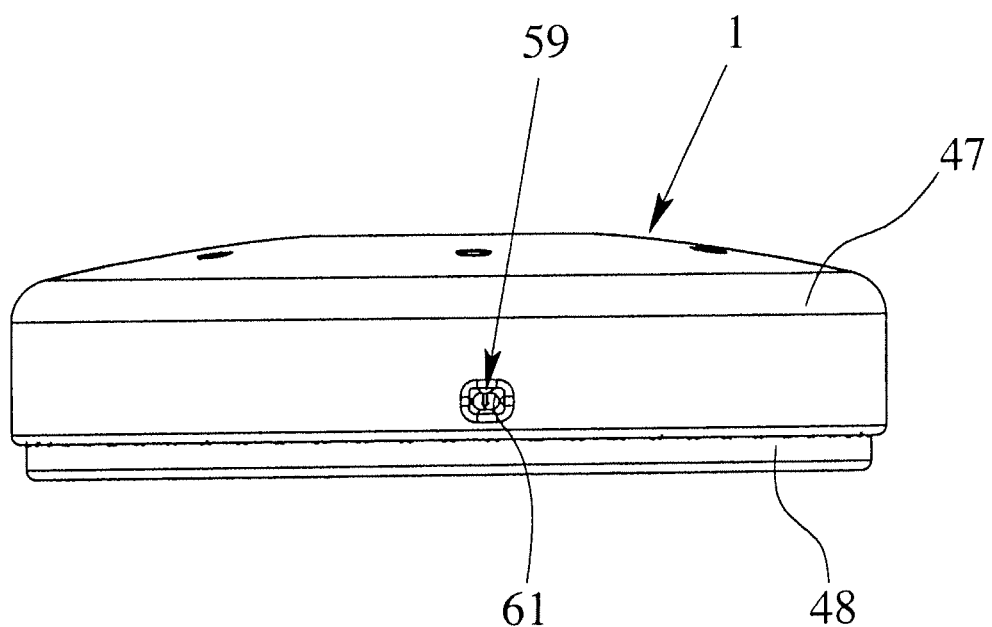
FIG. 20 is a side view, corresponding to FIG. 19, of the atomizer in the unlatched state.

FIG. 20 is a view corresponding to FIG. 19 that shows the atomizer 1 in the unlocked state, i.e., with the upper housing part 47 axially raised. In this position, the reservoir 3 has preferably been moved axially relative to the window 61 so that the scale 60 is not visible. Instead, preferably a symbol, particularly an arrow or the like, is indicated, to show the user how to operate it, namely by pressing the two housing parts 47 and 48 together as required. To this extent, the counter serves not only to count but also has another function and assists with the operation of the proposed atomizer 1.

The atomizer 1 according to the sixth embodiment may have a central or axial recess 62 in the housing 13 or upper housing part 47, as indicated in FIGS. 15 & 16. This recess 62 may be used for additional functions or devices.

Figure 21:
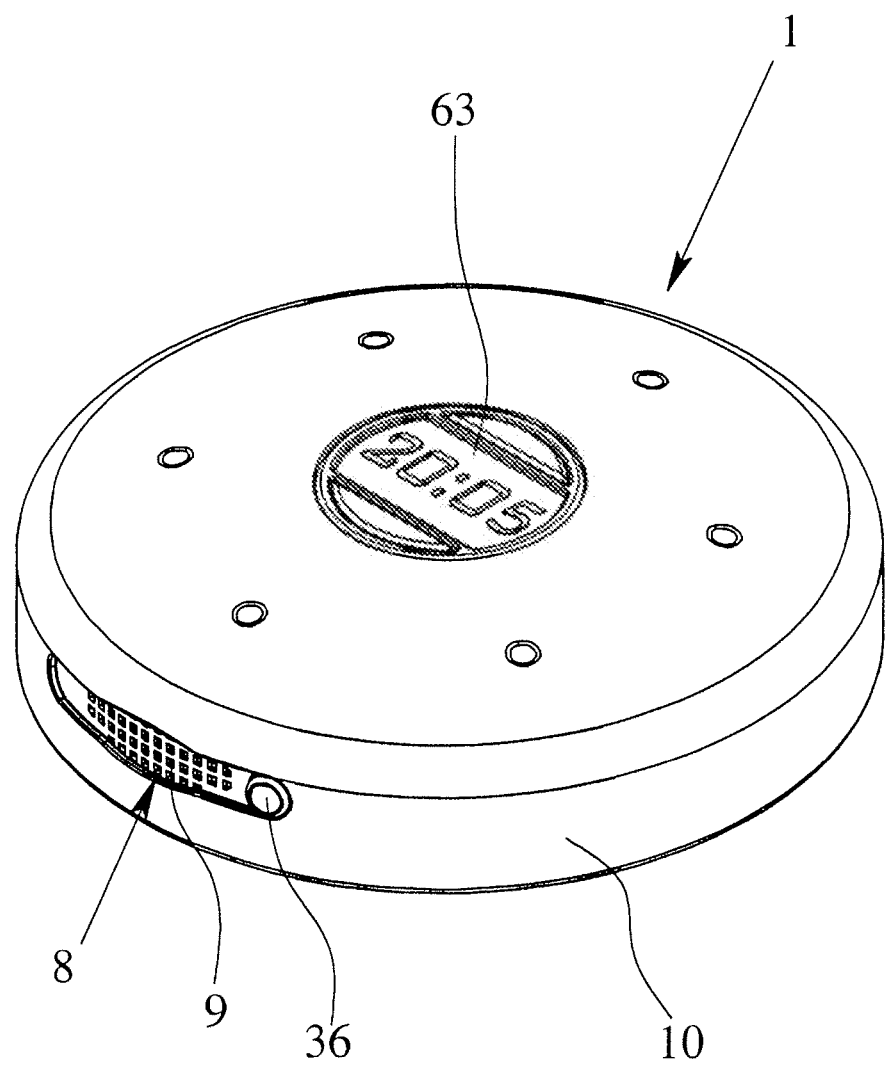
FIG. 21 is a perspective view of the atomizer according to FIG. 15 with a timer.

FIG. 21 shows an alternative embodiment of the atomizer 1 with a clock 63 or with a time measuring device. The clock 63 is preferably installed in the recess or otherwise integrated in the atomizer 1 or its housing 13. The clock 63 is, in particular, constructed so that a preferably optical, acoustic and/or vibratory signal can be emitted to remind the user to use the atomizer 1.

Figure 22:
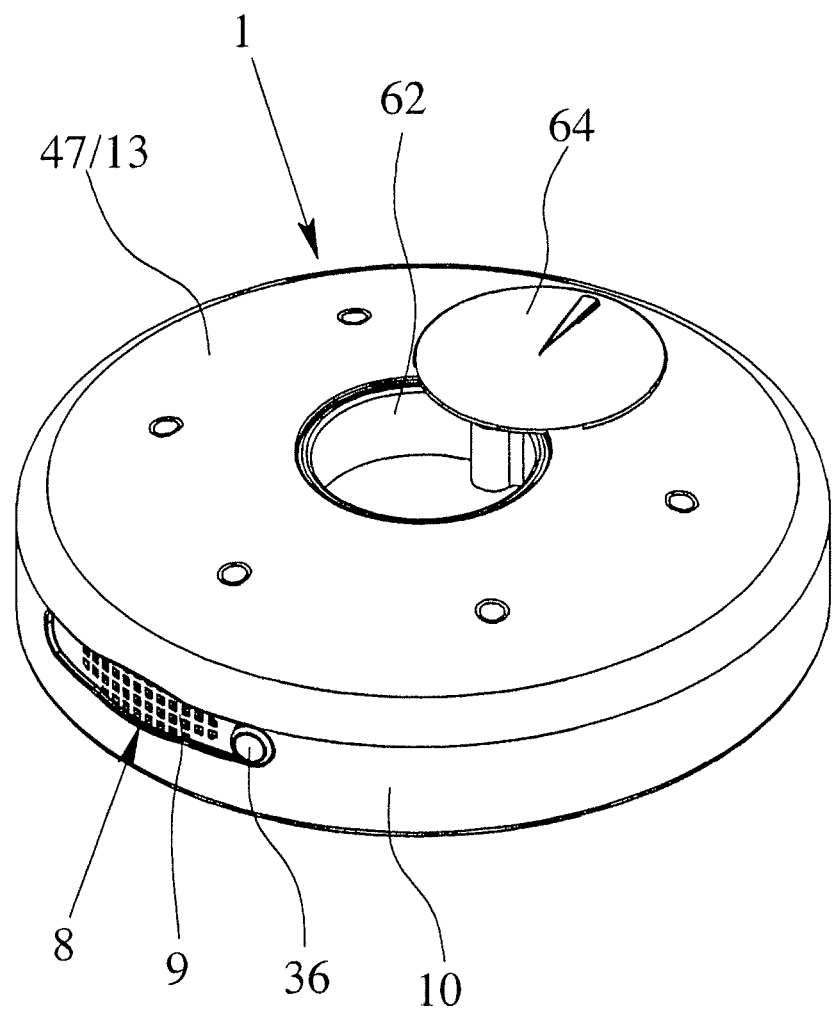
FIG. 22 is a perspective view of the atomizer according to FIG. 15 with a medicament receptacle.

FIG. 22 shows another alternative embodiment of the atomizer 1 with a closable chamber or other receptacle for medicaments or the like (not shown). In particular, the recess 62 is constructed to accommodate medicaments or the like and can be closed off, for example, by a lid 64 or other closure.

Figure 23:
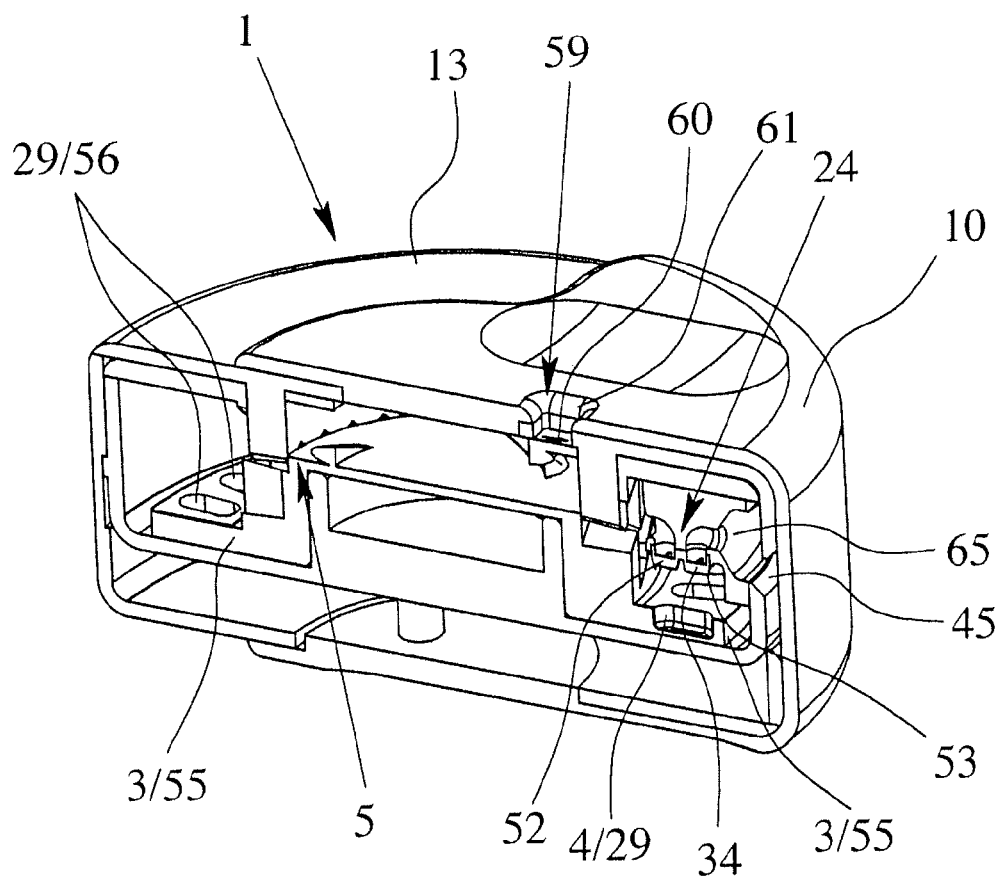
FIG. 23 is a schematic cross section of a proposed atomizer according to an eighth embodiment in the transportation position.

FIG. 23 shows in schematic section an eighth embodiment of the proposed atomizer 1 in the transportation position, namely with the cover 10 closed. The eighth embodiment is a passive atomizer 1, like the one in the seventh embodiment. The opening and closing and actuating of the atomizer 1 by rotating or pivoting the cover 10 corresponds however, in principle, to the first to third embodiments.

In the eighth embodiment, the reservoir 3 and connecting device 24 are constructed essentially as in the seventh embodiment. The connecting device 24 or the connecting element 34 thereof is axially movable by the opening and closing of the cover 10 by means of the gear (not shown in detail). In the transportation position, the connecting device 24 or the connecting element 34 thereof are moved axially away from the reservoir 3.

Figure 24:
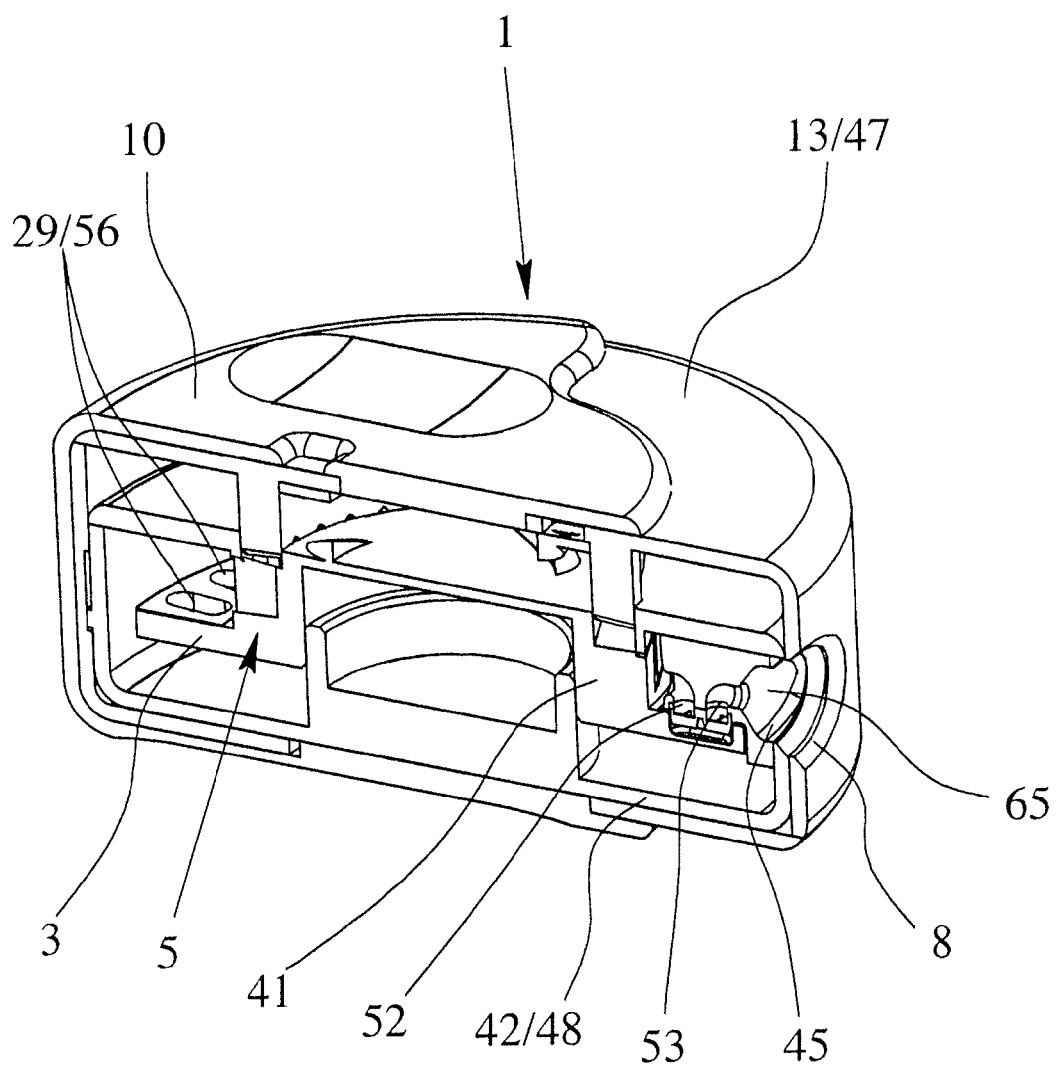
FIG. 24 is a schematic cross section of the atomizer according to FIG. 23 in the opened or activated state.

By opening the cover 10 (pivoting through preferably up to 180° approximately), first of all, the reservoir 3 is advanced or further rotated, and as the axial movement continues, the next receptacle 4 is opened by the connecting device 24, particularly pierced or otherwise attached by the connecting element 34. FIG. 24 shows this activated state in schematic section.

When a user or patient breathes in to inhale, a current of air is produced which is passed through the connecting element 34 through the receptacle 4 or the storage chamber 31, such as a blister pouch or the like, and in this way, the formulation 2 contained in the receptacle 4 is expelled and delivered through the adjoining mouthpiece 8.

To permit a simple and inexpensive construction, the inlet 52 and outlet 53 are preferably formed by a common component, particularly, the one-piece connecting element 34. Furthermore, the connecting element 34 preferably also has an outlet channel 65 adjacent to the outlet 53 and widening out in a funnel shape or other suitable manner, in particular. Thus, there is no need for a mouthpiece 8 in the conventional sense or an extension piece or the like as is often used with inhalers. Rather, it is sufficient to have a housing opening, and if necessary, a corresponding shaping of the housing 13, in order to form a compact, space-saving mouthpiece 8 for a user or patient.

Figure 25:
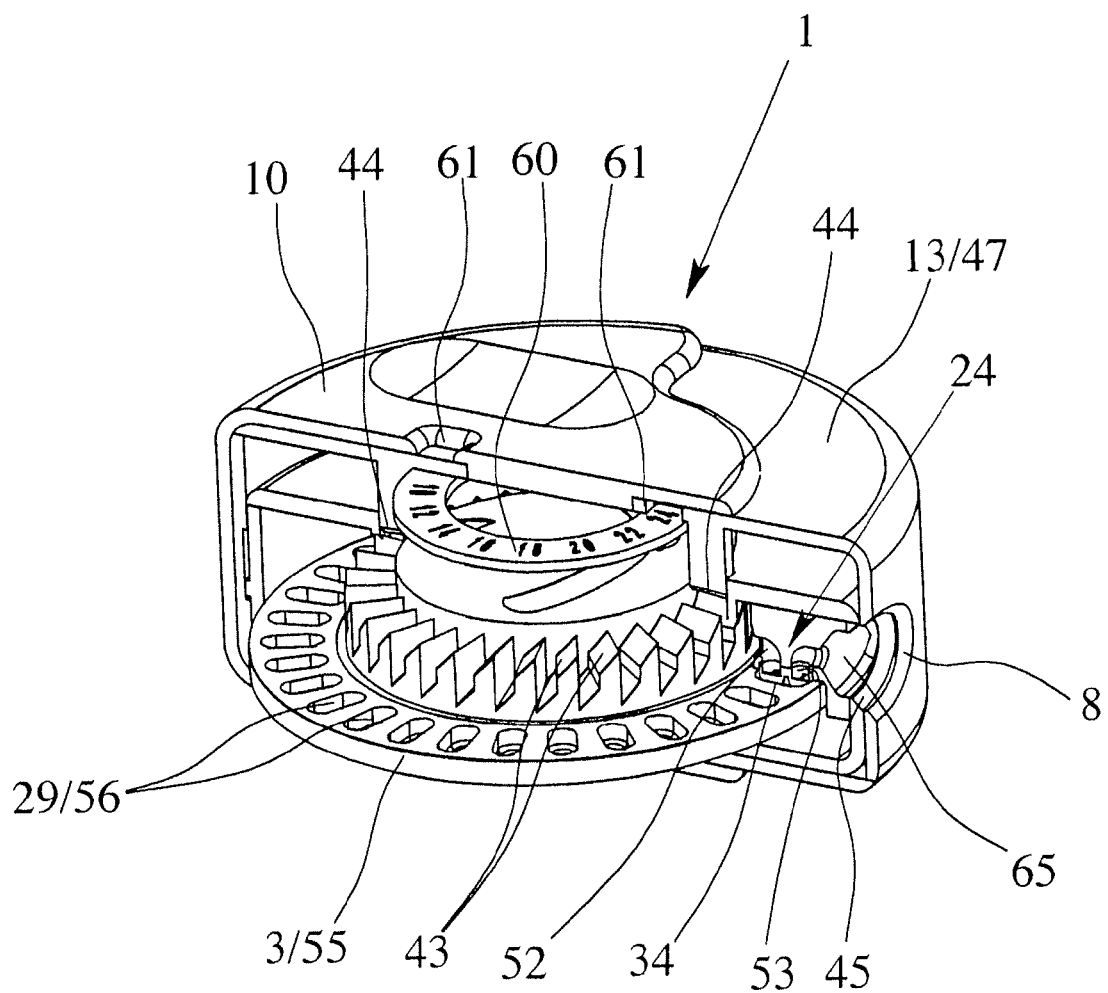
FIG. 25 is a schematic view of a transporting device of the atomizer according to FIG. 23.

FIG. 25 shows a schematic view which illustrates the transporting device 23 of the atomizer 1 according to the eighth embodiment. In particular, axial teeth 43 on the reservoir side and axially movable mating teeth 44 on the housing side—particularly together with the connecting device 24—cooperate so as to achieve the desired stepwise advancing or further rotation of the reservoir 3 by one receptacle 4, with each axial movement of the mating teeth 44 relative to the teeth 43 associated with the opening of the cover 10. In particular, the ballpoint pen principle mentioned previously comes into play again.

However, other constructional solutions are also possible in order to achieve the desired stepwise advancing or further rotation of the reservoir 3 from the movement of the cover 10 that accompanies opening and/or closing, particularly the pivoting movement and/or an axial movement derived therefrom.

In contrast to the seventh embodiment, in the eighth embodiment, the counter 59 is preferably arranged on the flat side or axial side of the atomizer 1, particularly with the window 61 being formed in the cover 10 and in the housing 13, so that the current status of the counter can preferably always be read off even when the cover 10 is closed.

In the eighth embodiment too, the reservoir 3 is again preferably provided with an annular carrier 55 for holding a blister arrangement, particularly a blister ring or the like. However, basically any desired type of reservoir 3—even, in particular, a reservoir 3 with inserts 28 for forming the receptacles 4—may be used here.

The eighth embodiment allows particularly easy operation as all that is required is to open the cover 10 in order to activate the atomizer 1, i.e., prepare it for atomization or inhalation. Even after atomization or inhalation, no other additional operations are required. Rather, it is necessary only to close the atomizer 1 or cover 10. When the cover 10 is closed the connecting device 24 or its connecting element 34 is moved axially away from the reservoir 3 or the receptacle 4 which was opened last, so that the transportation position shown in FIG. 23 is resumed.

Figure 26:
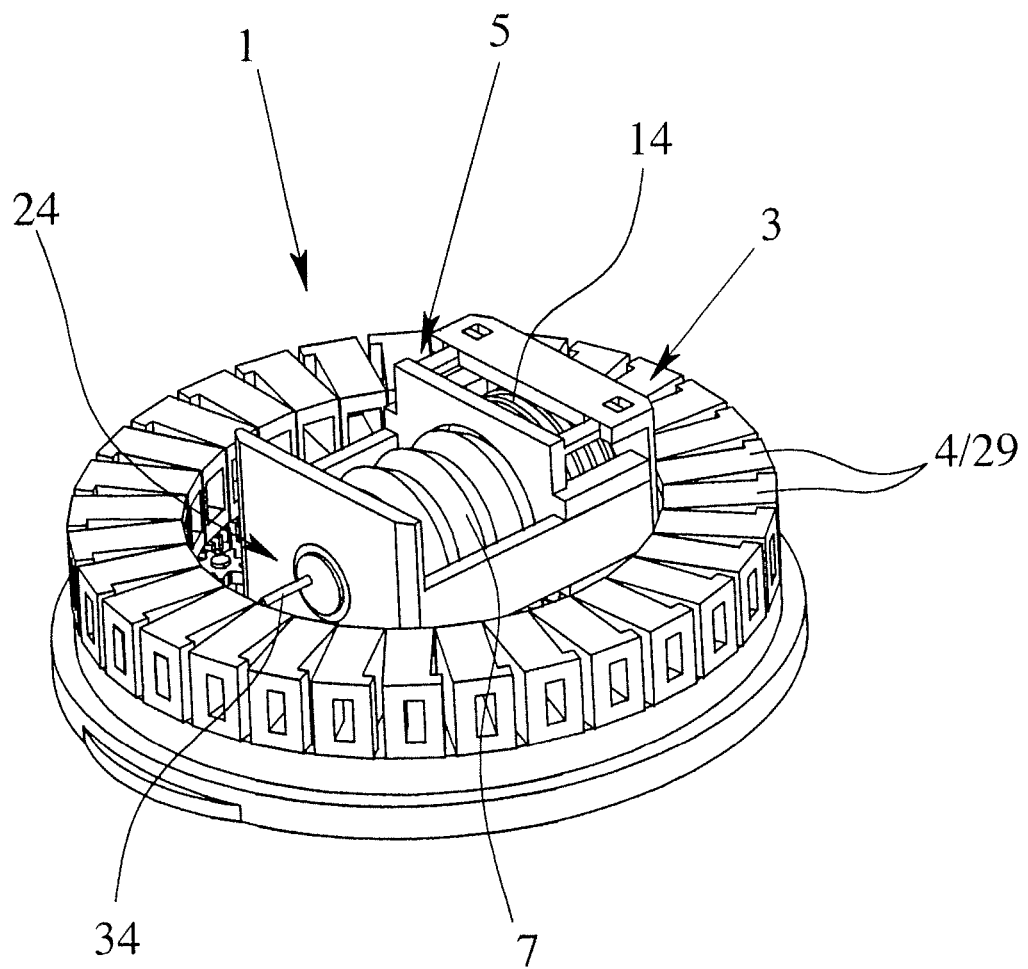
FIG. 26 is a schematic view of a part of an atomizer according to a ninth embodiment.

FIG. 26 shows a highly schematic rudimentary representation of the concept of a ninth embodiment of the proposed atomizer 1. The ninth embodiment relates to an active atomizer 1 having a delivery device 5 and an energy or spring store which are preferably arranged within the annular arrangement of the reservoir 3 or the receptacles 4, which are merely indicated by receiving chambers 29 in FIG. 26.

In the ninth embodiment, the delivery device 5 is again preferably constructed as a pump and is provided, in particular, with the bellows 7 which are preferably movable thereon in a radial direction for pumping, particularly are extendable and collapsible or compressible. The spring store or spring 14 is preferably arranged in this pumping direction behind the bellows 7, particularly on the side remote from the connecting device 24.

FIG. 26 shows the spring store or the spring 14 in the biased state with the bellows 7 extended. In this state, ambient air has already been taken in by the delivery device 5 or the bellows 7.

Figure 27:
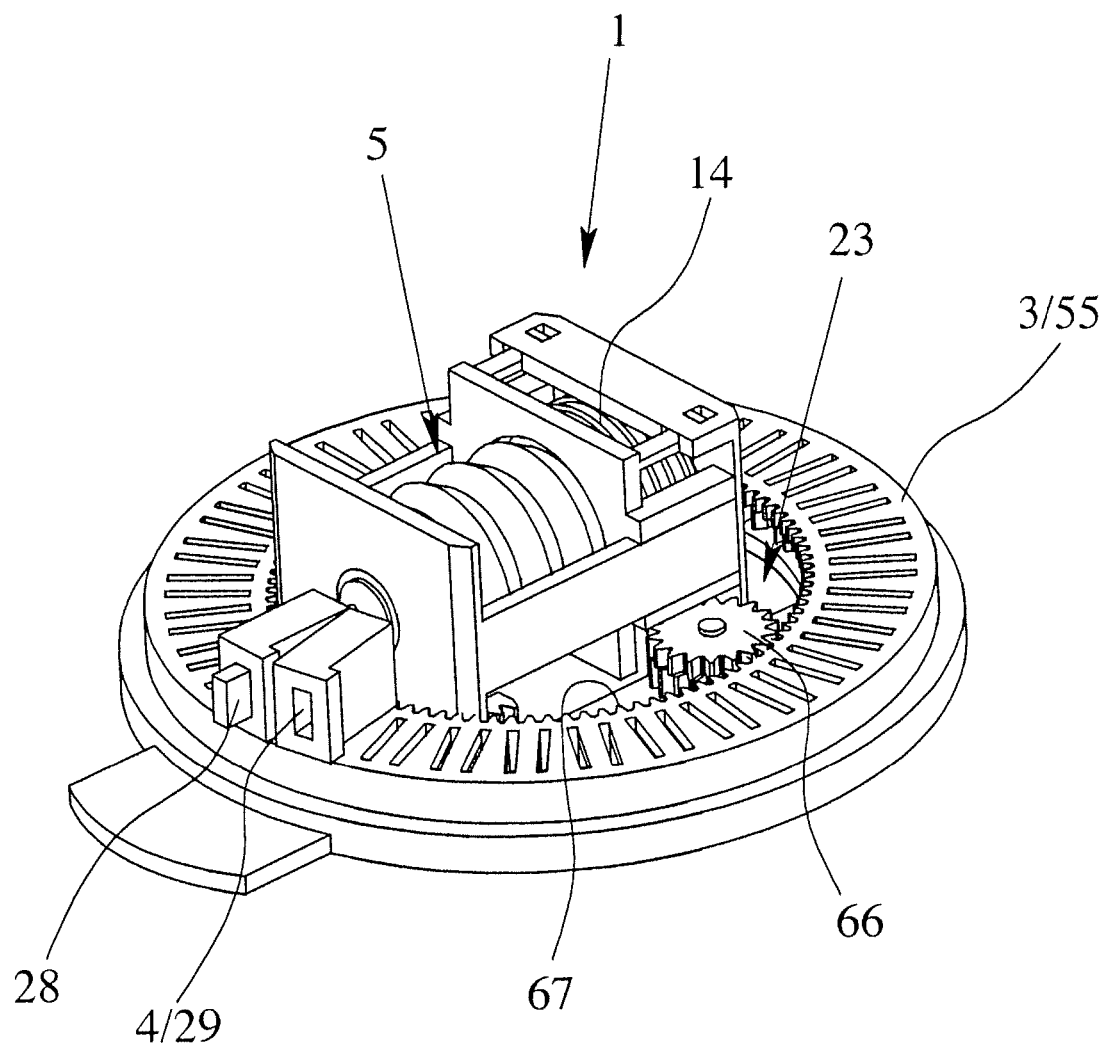
FIG. 27 is a view corresponding to FIG. 26 of the atomizer in an activated state.
Figure 28:
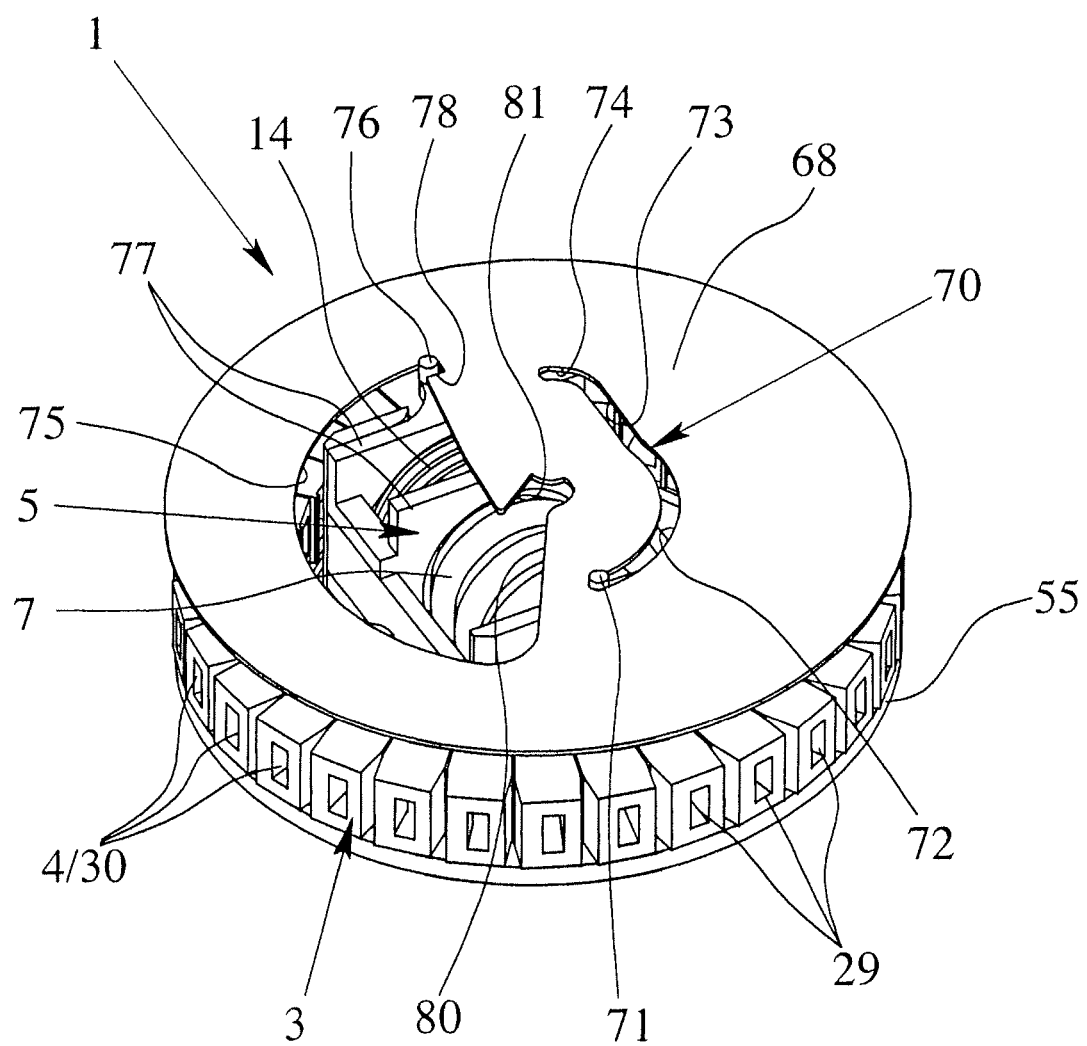
FIG. 28 is a schematic functional representation of an atomizer according to a tenth embodiment.
Figure 29:
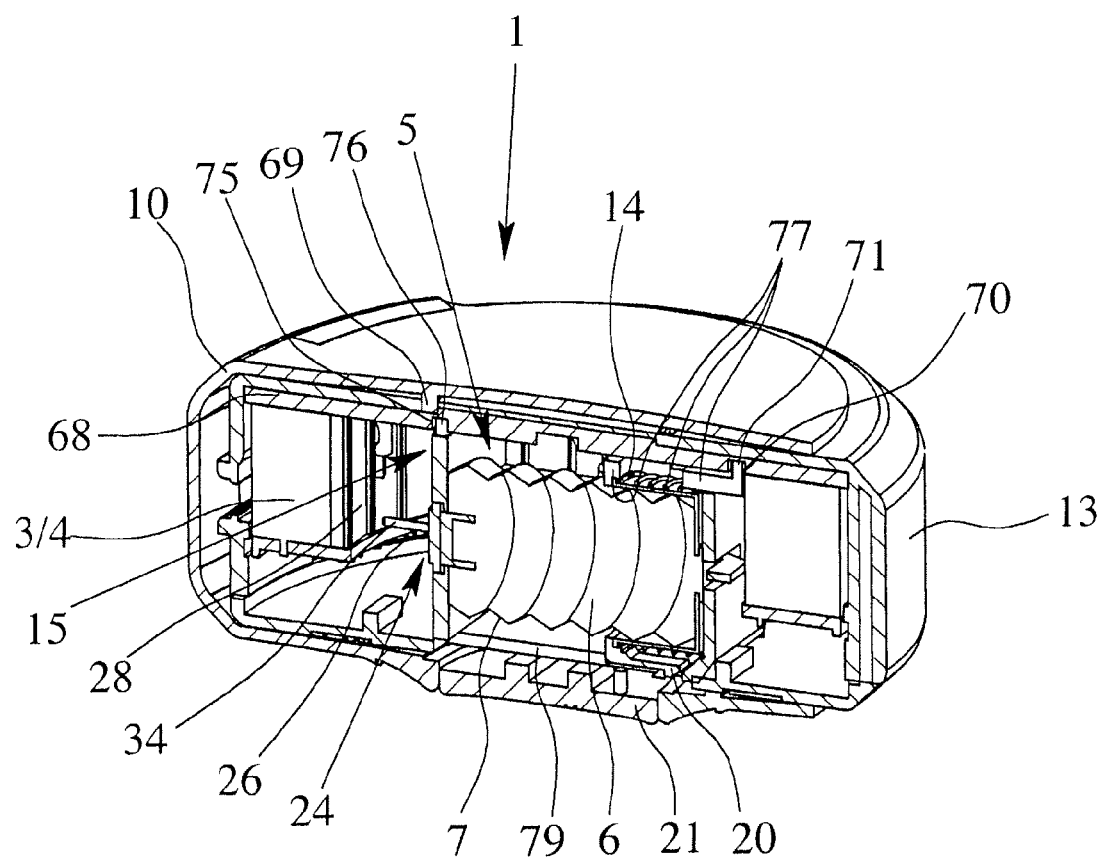
FIG. 29 is a schematic cross section of the atomizer according to FIG. 28.

The delivery device 5 with the spring store is preferably movable in the manner of a sled. In order to open the receptacle 4 which is to be used next, the delivery device 5 with the connecting device 24 or the connecting element 34 is, first of all, advanced radially so that the next receptacle 4 or the next insert 28 is radially pierced or connected by the delivery device 5 and moved radially outwards. This state is shown in the schematic representation in FIG. 27. Then, actuation takes place. By relaxing the spring 14 in the radial direction, the bellows 7 is compressed and the air contained therein flows through the connecting element 34 and the attached receptacle 4—particularly the attached insert 28—as a result of which the formulation 2 contained in the receptacle 4 or in the insert 28 is expelled. Then, the delivery device 5 and/or the connecting device 24 can be radially withdrawn again, in particular, by or radial movement. In addition, the spring 14 is biased once again due to the radial movement, wherein the bellows 7 is extended and the delivery medium, here air, is sucked into the bellows 7. The spring 14 is secured or latched in the biased position, in particular, to the sled.

With the opposite radial movement, the next receptacle 4 or insert 28 can be pierced and, in particular, pushed radially outwardly to open its respective sealing. During this radial movement, the spring 24 remains compressed or tensioned and the bellows 7 remains extended. Thus, the activated state of the atomizer 1 is achieved.

Preferably, with actuating of the actuating element (not shown), the spring 14 is released to compress the bellows 7, i.e., to actuate the pump, so that the compressed delivery medium, i.e., air, is forced through the insert 28 to deliver or discharge or atomize or de-agglomerate the respective dose of formulation 2 and to generate the desired spray of the formulation 2.

Part of the radial movement is preferably also used to index or move the reservoir 3 to the next receptacle 4, i.e., to actuate the transporting device 23.

The transporting device 23 in the ninth embodiment preferably engages internally on the reservoir 3, particularly via a pinion 66 which preferably engages in inner teeth 67 of the reservoir 3.

It is noted that the connecting device 24 and the pump 5 preferably form a unit or are interconnected.

The connecting element 34 is connected to the sled and/or pump 5 and/or bellows 7.

In the ninth embodiment, the receptacles 4/receiving chambers 29 form preferably separate parts that are mounted on the preferably ring-like carrier 55, in particular, in a form-fit and/or rigid manner. The receiving chambers 29 or receptacles 4 are preferably separately or individually sealed by respective seals and/or preferably at least on its outer circumferential periphery (not shown in FIGS. 26 & 27).

FIG. 28 shows, in a similar very schematic, rudimentary representation, a tenth embodiment of the proposed atomizer 1. The tenth embodiment is related to the ninth embodiment, and in particular, is similar to it, most preferably with respect to the arrangement and/or function of the delivery device 5 and connecting device 24, and therefore, no explanation of these aspects is required.

FIG. 29 shows the atomizer 1 according to the tenth embodiment in schematic section, in contrast to FIG. 28, with the housing 13 and the preferably rotatable or pivotable cover 10.

The tenth embodiment allows a pivoting or rotary movement, particularly of the cover 10, to be converted into a linear and/or radial movement in order to actuate the delivery device 5 and/or connecting device 24, most preferably in order to move the connecting element 34. In particular, a sliding and/or automatically geared coupling or control is obtained.

In the embodiment shown, the atomizer 1 has at least one control element 68 which is constructed, in particular, in the manner of a disc (cf. FIG. 28). The control element 68 is preferably rotationally coupled to the cover 10 (in the embodiment shown via an axial engagement 69 as indicated in FIG. 29) or is formed by the cover element 10, for example.

Particularly preferably, the control element 68 forms a sliding guide or a number of sliding guides in order to actuate in particular, both the delivery device 5 and the connecting device 24 or its connecting element 34 in the desired or necessary manner. However, it is theoretically also possible to use separate control elements 68, sliding guides and/or other geared connections to control and actuate the delivery device 5, on the one hand, and the connecting device 24 or its connecting element 34, on the other hand, and/or for different sections of the movements.

In the embodiment shown, a first control cam or sliding guide 70 is provided for preferably linear or radial movement of the connecting device 24 or of the slide 79 formed by the delivery device 5 and/or connecting device 24. For this purpose, in particular, a first engaging element 71 engages in the first sliding guide 70. Preferably, the first engaging element 71 is rigidly connected to the connecting device 24 or its connecting element 34, directly or indirectly.

The first sliding guide 70 is shown in FIG. 28 as an opening. However, it may also be a recess or groove or the like, in particular, as shown in FIG. 29. The path of the first sliding guide 70 determines the geared coupling or the dependency of the linear movement which may also extend circumferentially and/or radially, on the rotary movement. In the embodiment shown, the first sliding guide 70 comprises a first section 72, particularly extending over a circumference, an adjoining second, preferably linear section 73 and/or one which has a radial component, and/or a third section 74 which in particular, again extends over a circumference.

Accordingly, during actuation, i.e., pivoting, of the cover 10 out of the position shown in FIGS. 28 & 29 (closed position or transportation position), first of all, in the course of the first section 72, there is no linear or radial movement of the connecting device 24 or slide 79. Only further along the second section 73 does a linear or radial movement take place, of the slide 79 or connecting device 24, in the embodiment shown, so that the connecting element 34 comes into contact with the next receptacle 4, particularly engages in the next receptacle 4 or the next insert 28, most preferably produces a fluidic connection between the delivery device 5 or the connecting element 34 and the storage chamber 31, and optionally, moves the insert 28 through the opening 30, particularly by radially advancing it, in order to open the opening 30. The atomizer 1 assumes the activated position.

During the transition from the closed state to the activated state, the delivery device 5 or the spring store or the spring 14 is preferably already under tension. Therefore, the actuating element 21 can now be actuated, so that the formulation 2 is delivered, particularly by deflecting a locking arm 20 and thereby releasing the spring 14 or the bellows 7 and compressing the pump chamber 6, as a result of which, the formulation 2 is expelled or delivered and in particular, atomized by the delivery medium in the desired manner, as explained previously.

In the embodiment shown, the cover 10 or the control element 68 preferably serves simultaneously to actuate the delivery device 5, particularly to bias the spring store or the spring 14. The control element 68 comprises, for this purpose, a second control cam or sliding guide 75, with which a second engaging element 76 cooperates, in particular which, in the embodiment shown, is associated with the delivery device 5 or spring store or spring 14, particularly a radially or linearly movable abutment 77 of the spring 14, or is firmly connected thereto, either directly or indirectly.

Particularly preferably, the abutment 77 is guided slidably or in the manner of a sled on the delivery device 5 or on the slide 79, which in turn is slidable in the manner of a sled in the direction of movement—in this case the radial direction—and in particular, holds or carries the connecting device 24 or the connecting element 34 thereof.

FIG. 29 shows the spring 14 in the biased position (in this case, the compressed state). The abutment 77 is held in the biased position by means of at least the locking arm 20. The second sliding guide 75 is preferably constructed in the embodiment shown such that in the closed position or transportation position the spring store or spring 14 is secured against unintentional relaxation, in particular, by a shoulder 78 which blocks radial movement of the second engagement 76 in this position.

When the actuating element 21 is actuated, the locking arm 20 is deflected out or the locking engagement is undone and the spring store or spring 14 is relaxed or the delivery device 5 is triggered. Then, the spring 14 compresses the bellows 7 or the pump chamber 6 in the manner described previously—in the embodiment shown—in linear fashion or in the radial direction. Accordingly, the formulation 2 (not shown in FIGS. 28 & 29) is then delivered, and in particular, atomized from the connected receptacle 4 or the connected insert 28, as already explained with reference to the other embodiments.

During the relaxation, the second engaging element 76 moves, in particular, towards the center of the atomizer 1 or control element 68 or towards the rotation axis of the cover 10, and optionally beyond. The second sliding guide 75 is correspondingly freely cut to allow this movement. In the embodiment shown, this movement extends essentially along a radial section 80 of the second sliding guide 75.

In the embodiment shown, particularly during the closing or moving back of the cover 10, the control element 68 is turned back or the spring store or spring 14 is put under tension again.

As the control element 68 is moved back or turned back from the position in the activated state (preferably rotated through 90° to 180° relative to the position in FIGS. 28 & 29), the abutment 77 is held back via the second engaging element 76 over a certain section of the opposing radial movement of the slide 79 or first engaging element 71 by a retaining section 81 of the second sliding guide 75, so that in this section of the movement the spring store or spring 14 is biased again and the bellows 7 is again extended, in particular, until latching takes place by means of the locking arm 20. During this movement, the connecting element 34 is preferably at least partly withdrawn at the same time from the attached receptacle 4 or the attached insert 28.

In the course of the further linear or radial movement, the delivery device 5, connecting device 24, connecting element 34 and the slide 79 together with the biased spring 14 are moved back into the starting position shown in FIGS. 28 & 29.

The sequence of movements described above is carried out in the embodiment shown particularly by closing the cover 10 and, in association therewith, turning back the control element 68.

FIG. 29, in turn, shows the preferably annular reservoir 3 in purely schematic form. In connection with this, reference may be made, in particular, to the remarks relating to the other embodiments.

During the opening movement and/or closing movement of the cover 10 or the rotation of the control element 68, the transporting device 23 not shown relative to the tenth embodiment can preferably be actuated in order to advance the reservoir 3 to the next receptacle 4. This is done, in particular, by means of a corresponding or suitable geared coupling or the like. For example, axial displacement of the reservoir 3 may be carried out for this purpose, as explained hereinbefore, the advance being carried out in the circumferential direction, or in particular, by means of a control cam 26 or the like preferably on the housing side. In particular, or alternatively, a geared coupling, particularly by means of a thread, may be used as in the other embodiments.

Individual features and aspects of the individual embodiments may also be combined with one another as desired or used in other constructions of atomizers, inhalers, dispensers or the like.

In the present invention the term "atomizer" is preferably to be interpreted very broadly so as to include other delivery devices, dispensers or the like, while the formulation 2 or other medium or fluid need only be atomized if required and may optionally also be delivered in a different form.

Some preferred ingredients and/or compositions of the preferably medicinal formulation 2 are listed below. As already mentioned, they are, in particular, powders or liquids in the broadest sense. Particularly preferably, the formulation 2 contains the following:

The compounds listed below may be used in the device according to the invention on their own or in combination. In the compounds mentioned below, W is a pharmacologically active substance and is selected (for example) from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined and used in the device according to the invention. Combinations of W might be, for example:

W denotes a betamimetic, combined with an anticholinergic, corticosteroid, PDE4-inhibitor, EGFR-inhibitor or LTD4-antagonist, W denotes an anticholinergic, combined with a betamimetic, corticosteroid, PDE4-inhibitor, EGFR-inhibitor or LTD4-antagonist, W denotes a corticosteroid, combined with a PDE4-inhibitor, EGFR-inhibitor or LTD4-antagonist, W denotes a PDE4-inhibitor, combined with an EGFR-inhibitor or LTD4-antagonist W denotes an EGFR-inhibitor, combined with an LTD4-antagonist.4

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide
5-[2-(5.6-diethyl-indan-2-ylamino)-1-hydroxy-ethyl]-8-hydroxy-1H-quinolin-2-one
4-hydroxy-7-[2-{[2-{[3-(2-phenylethoxy)propyl] sulphonyl}ethyl]-amino}ethyl]-2(3H)-benzothiazolone
1-(2-fluoro-4-hydroxyphenyl)-2-[4-(1-benzimidazolyl)-2-methyl-2-butylamino]ethanol
1-[3-(4-methoxybenzyl-amino)-4-hydroxyphenyl]-2-[4-(1-benzimidazolyl)-2-methyl-2-butylamino]ethanol
1-[2H-5-hydroxy-3-oxo-4H-1,4-benzoxazin-8-yl]-2-[3-(4-N,N-dimethylaminophenyl)-2-methyl-2-propylamino] ethanol
1-[2H-5-hydroxy-3-oxo-4H-1,4-benzoxazin-8-yl]-2-[3-(4-methoxyphenyl)-2-methyl-2-propylamino]ethanol
1-[2H-5-hydroxy-3-oxo-4H-1,4-benzoxazin-8-yl]-2-[3-(4-n-butyloxyphenyl)-2-methyl-2-propylamino]ethanol
1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol
5-hydroxy-8-(1-hydroxy-2-isopropylaminobutyl)-2H-1,4-benzoxazin-3-(4H)-one
1-(4-amino-3-chloro-5-trifluoromethylphenyl)-2-tert.-butylamino)ethanol
6-hydroxy-8-{1-hydroxy-2-[2-(4-methoxy-phenyl)-1,1-dimethyl-ethylamino]-ethyl}-4H-benzo[1,4]oxazin-3-one
6-hydroxy-8-{1-hydroxy-2-[2-(ethyl 4-phenoxy-acetate)-1,1-dimethyl-ethylamino]-ethyl}-4H-benzo[1,4]oxazin-3-one
6-hydroxy-8-{1-hydroxy-2-[2-(4-phenoxy-acetic acid)-1,1-dimethyl-ethylamino]-ethyl}-4H-benzo[1,4]oxazin-3-one
8-{2-[1,1-dimethyl-2-(2,4,6-trimethylphenyl)-ethylamino]-1-hydroxy-ethyl}-6-hydroxy-4H-benzo[1,4]oxazin-3-one
6-hydroxy-8-{1-hydroxy-2-[2-(4-hydroxy-phenyl)-1,1-dimethyl-ethylamino]-ethyl}-4H-benzo[1,4]oxazin-3-one
6-hydroxy-8-{1-hydroxy-2-[2-(4-isopropyl-phenyl)-1,1-dimethyl-ethylamino]-ethyl}-4H-benzo[1,4]oxazin-3-one
8-{2-[2-(4-ethyl-phenyl)-1,1-dimethyl-ethylamino]-1-hydroxy-ethyl}-6-hydroxy-4H-benzo[1,4]oxazin-3-one
8-{2-[2-(4-ethoxy-phenyl)-1,1-dimethyl-ethylamino]-1-hydroxy-ethyl}-6-hydroxy-4H-benzo[1,4]oxazin-3-one
4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid
8-{2-[2-(3,4-difluoro-phenyl)-1,1-dimethyl-ethylamino]-1-hydroxy-ethyl}-6-hydroxy-4H-benzo[1,4]oxazin-3-one
1-(4-ethoxy-carbonylamino-3-cyano-5-fluorophenyl)-2-(tert-butylamino)ethanol
2-hydroxy-5-(1-hydroxy-2-{2-[4-(2-hydroxy-2-phenyl-ethylamino)-phenyl]-ethylamino}-ethyl)-benzaldehyde
N-[2-hydroxy-5-(1-hydroxy-2-{2-[4-(2-hydroxy-2-phenyl-ethylamino)-phenyl]-ethylamino}-ethyl)-phenyl]-formamide
8-hydroxy-5-(1-hydroxy-2-{2-[4-(6-methoxy-biphenyl-3-ylamino)-phenyl]-ethylamino}-ethyl)-1H-quinolin-2-one
8-hydroxy-5-[1-hydroxy-2-(6-phenethylamino-hexylamino)-ethyl]-1H-quinolin-2-one
5-[2-(2-{4-[4-(2-amino-2-methyl-propoxy)-phenylamino]-phenyl}-ethylamino)-1-hydroxy-ethyl]-8-hydroxy-1H-quinolin-2-one
[3-(4-{6-[2-hydroxy-2-(4-hydroxy-3-hydroxymethyl-phenyl)-ethylamino]-hexyloxy}-butyl)-5-methyl-phenyl]-urea
4-(2-{6-[2-(2,6-dichloro-benzyloxy)-ethoxy]-hexylamino}-1-hydroxy-ethyl)-2-hydroxymethyl-phenol
3-(4-{6-[2-hydroxy-2-(4-hydroxy-3-hydroxymethyl-phenyl)-ethylamino]-hexyloxy}-butyl)-benzylsulphonamide
3-(3-{7-[2-hydroxy-2-(4-hydroxy-3-hydroxymethyl-phenyl)-ethylamino]-heptyloxy}-propyl)-benzylsulphonamide
4-(2-{6-[4-(3-cyclopentanesulphonyl-phenyl)-butoxy]-hexylamino}-1-hydroxy-ethyl)-2-hydroxymethyl-phenol
N-Adamantan-2-yl-2-(3-{2-[2-hydroxy-2-(4-hydroxy-3-hydroxymethyl-phenyl)-ethylamino]-propyl}-phenyl)-acetamide Optionally, in the form of the racemates, enantiomers, diastereomers thereof and optionally in the form of the pharmacologically acceptable acid addition salts, solvates or hydrates thereof. According to the invention, the acid addition salts of the betamimetics are preferably selected from among the hydrochloride, hydrobromide, hydroxide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts, the chlorides, bromides, iodides and methanesulphonates are particularly preferred.

Other preferred anticholinergics are selected from among the salts of formula

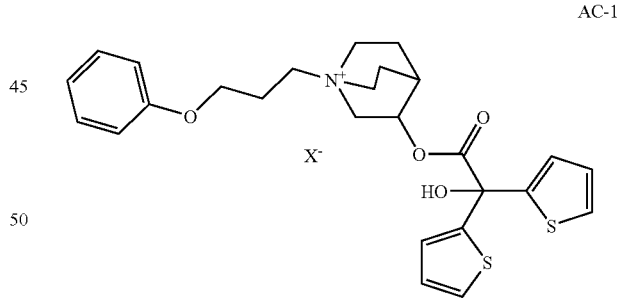

AC-1 wherein X⁻ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably, an anion selected from among the fluoride, chloride, bromide, methanesulphonate and p-toluenesulphonate, particularly preferably, bromide, optionally in the form of the racemates, enantiomers or hydrates thereof. Of particular importance are those pharmaceutical combinations which contain the enantiomers of formula AC-1-en AC-1

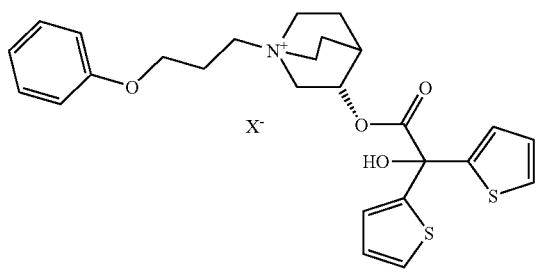

AC-1-en wherein X⁻ may have the above-mentioned meanings. Other preferred anticholinergics are selected from the salts of formula AC-2

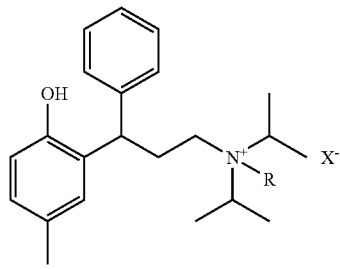

AC-2 wherein R denotes either methyl or ethyl and wherein X⁻ may have the above-mentioned meanings. In an alternative embodiment the compound of formula AC-2 may also be present in the form of the free base AC-2-base.

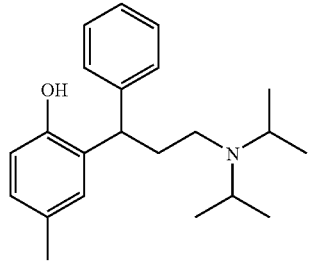

AC-2-base

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzoate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate-methobromide;
scopine 9-methyl-xanthene-9-carboxylate-methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide, The above-mentioned compounds may also be used as salts within the scope of the present invention, wherein instead of the methobromide the salts metho-X are used, wherein X may have the meanings given hereinbefore for X⁻.

As corticosteroids, it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and
(S)-fluoromethyl 6,9-difluoro-17-[(2-furanylcarbonyl)oxy]-11-hydroxy-16-methyl-3-oxo-androsta-1,4-diene-17-carbothionate
(S)-(2-oxo-tetrahydro-furan-3S-yl)6,9-difluoro-11-hydroxy-16-methyl-3-oxo-17-propionyloxy-androsta-1,4-diene-17-carbothionate,
cyanomethyl 6α,9α-difluoro-11β-hydroxy-16α-methyl-3-oxo-17α-(2,2,3,3-tertamethylcyclopropylcarbonyl)oxy-androsta-1,4-diene-17β-carboxylate
optionally, in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example, sodium or potassium salts, sulphobenzoates, phosphates, isonicotinates, acetates, dichloroacetates, propionates, dihydrogen phosphates, palmitates, pivalates or furoates. PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, Cl-1018, CDC-801, CDC-3052, D-22888, YM-58997, Z-15370 and N-(3,5-dichloro-1-oxo-pyridin-4-yl)-4-difluoromethoxy-3-cyclopropylmethoxybenzamide
(−)$_p$-[(4aR*, 10bS*)-9-ethoxy-1,2,3,4,4a,10b-hexahydro-8-methoxy-2-methylbenzo[s][1,6]naphthyridin-6-yl]-N,N-diisopropylbenzamide
(R)-(+)-1-(4-bromobenzyl)-4-[(3-cyclopentyloxy)-4-methoxyphenyl]-2-pyrrolidone
3-(cyclopentyloxy-4-methoxyphenyl)-1-(4-N'-[N-2-cyano-S-methyl-isothioureido]benzyl)-2-pyrrolidone cis[4-cyano-4-(3-cyclopentyloxy-4-methoxyphenyl)cyclo-
hexane-1-carboxylic acid]2-carbomethoxy-4-cyano-4-(3-
cyclopropylmethoxy-4-difluoromethoxy-phenyl)cyclo-
hexan-1-one
cis[4-cyano-4-(3-cyclopropylmethoxy-4-difluoromethox-
yphenyl)cyclohexan-1-ol](R)-(+)-ethyl[4-(3-cyclopenty-
loxy-4-methoxyphenyl)pyrrolidin-2-ylidene]acetate
(S)-(−)-ethyl[4-(3-cyclopentyloxy-4-methoxyphenyl)pyrro-
lidin-2-ylidene]acetate
9-cyclopentyl-5,6-dihydro-7-ethyl-3-(2-thienyl)-9H-pyra-
zolo[3,4-c]-1,2,4-triazolo[4,3-a]pyridine
9-cyclopentyl-5,6-dihydro-7-ethyl-3-(tert-butyl)-9H-pyra-
zolo[3,4-c]-1,2,4-triazolo[4,3-a]pyridine
optionally, in the form of the racemates, enantiomers or diastereomers thereof and optionally in the form of the pharmacologically acceptable acid addition salts thereof, the solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and
1-((((R)-(3-(2-(6,7-difluoro-2-quinolinyl)ethenyl)phenyl)-
3-(2-(2-hydroxy-2-propyl)phenyl)thio)methylcyclopro-
pane-acetic acid,
1-(((1(R)-3(3-(2-(2,3-dichlorothieno[3,2-b]pyridin-5-yl)-
(E)-ethenyl)phenyl)-3-(2-(1-hydroxy-1-methylethyl)phe-
nyl)propyl)thio)methyl)cyclopropaneacetic acid
[2-[[2-(4-tert-butyl-2-thiazolyl)-5-benzofuranyl]oxymethyl]
phenyl]acetic acid
optionally, in the form of the racemates, enantiomers or diastereomers thereof and optionally in the form of the pharmacologically acceptable acid addition salts, solvates and/or hydrates thereof. According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example, sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and
4-[(3-chloro-4-fluorophenyl)amino]-6-{[4-(morpholin-4-
yl)-1-oxo-2-buten-1-yl]-amino}-7-cyclopropylmethoxy-
quinazoline
4-[(3-chloro-4-fluorophenyl)amino]-6-{[4-(N,N-diethy-
lamino)-1-oxo-2-buten-1-yl]amino}-7-cyclopropyl-
methoxy-quinazoline
4-[(3-chloro-4-fluorophenyl)amino]-6-{[4-(N,N-dimethy-
lamino)-1-oxo-2-buten-1-yl]amino}-7-cyclopropyl-
methoxy-quinazoline
4-[(R)-(1-phenyl-ethyl)amino]-6-{[4-(morpholin-4-yl)-1-
oxo-2-buten-1-yl]-amino}-7-cyclopentyloxy-quinazoline
4-[(3-chloro-4-fluoro-phenyl)amino]-6-{[4-((R)-6-methyl-
2-oxo-morpholin-4-yl)-1-oxo-2-buten-1-yl]amino}-7-cy-
clopropylmethoxy-quinazoline
4-[(3-chloro-4-fluoro-phenyl)amino]-6-{[4-((R)-6-methyl-
2-oxo-morpholin-4-yl)-1-oxo-2-buten-1-yl]amino}-7-
[(S)-(tetrahydrofuran-3-yl)oxy]-quinazoline
4-[(3-chloro-4-fluoro-phenyl)amino]-6-{[4-((R)-2-meth-
oxymethyl-6-oxo-morpholin-4-yl)-1-oxo-2-buten-1-yl]
amino}-7-cyclopropylmethoxy-quinazoline
4-[(3-chloro-4-fluoro-phenyl)amino]-6-[2-((S)-6-methyl-2-
oxo-morpholin-4-yl)-ethoxy]-7-methoxy-quinazoline
4-[(3-chloro-4-fluorophenyl)amino]-6-({4-[N-(2-methoxy-
ethyl)-N-methyl-amino]-1-oxo-2-buten-1-yl}amino)-7-
cyclopropylmethoxy-quinazoline
4-[(3-chloro-4-fluorophenyl)amino]-6-{[4-(N,N-dimethy-
lamino)-1-oxo-2-buten-1-yl]amino}-7-cyclopentyloxy-
quinazoline
4-[(R)-(1-phenyl-ethyl)amino]-6-{[4-(N,N-to-(2-methoxy-
ethyl)-amino]-1-oxo-2-buten-1-yl}amino}-7-cyclopropy-
lmethoxy-quinazoline
4-[(R)-(1-phenyl-ethyl)amino]-6-({4-[N-(2-methoxy-
ethyl)-N-ethyl-amino]-1-oxo-2-buten-1-yl}amino)-7-cy-
clopropylmethoxy-quinazoline
4-[(R)-(1-phenyl-ethyl)amino]-6-({4-[N-(2-methoxy-
ethyl)-N-methyl-amino]-1-oxo-2-buten-1-yl}amino)-7-
cyclopropylmethoxy-quinazoline
4-[(R)-(1-phenyl-ethyl)amino]-6-({4-[N-(tetrahydropyran-
4-yl)-N-methyl-amino]-1-oxo-2-buten-1-yl}amino)-7-cy-
clopropylmethoxy-quinazoline
4-[(3-chloro-4-fluorophenyl)amino]-6-{[4-(N,N-dimethy-
lamino)-1-oxo-2-buten-1-yl]amino}-7-((R)-tetrahydrofu-
ran-3-yloxy)-quinazoline
4-[(3-chloro-4-fluorophenyl)amino]-6-{[4-(N,N-dimethy-
lamino)-1-oxo-2-buten-1-yl]amino}-7-((S)-tetrahydrofu-
ran-3-yloxy)-quinazoline
4-[(3-chloro-4-fluorophenyl)amino]-6-({4-[N-(2-methoxy-
ethyl)-N-methyl-amino]-1-oxo-2-buten-1-yl}amino)-7-
cyclopentyloxy-quinazoline
4-[(3-chloro-4-fluorophenyl)amino]-6-{[4-(N-cyclopropyl-
N-methyl-amino)-1-oxo-2-buten-1-yl]amino}-7-cyclo-
pentyloxy-quinazoline
4-[(3-chloro-4-fluorophenyl)amino]-6-{[4-(N,N-dimethy-
lamino)-1-oxo-2-buten-1-yl]amino}-7-[(R)-(tetrahydro-
furan-2-yl)methoxy]-quinazoline
4-[(3-chloro-4-fluorophenyl)amino]-6-{[4-(N,N-dimethy-
lamino)-1-oxo-2-buten-1-yl]amino}-7-[(S)-(tetrahydro-
furan-2-yl)methoxy]-quinazoline
4-[(3-ethynyl-phenyl)amino]-6,7-to-(2-methoxy-ethoxy)-
quinazoline
4-[(3-chloro-4-fluorophenyl)amino]-7-[3-(morpholin-4-yl)-
propyloxy]-6-[(vinyl-carbonyl)amino]-quinazoline
4-[(R)-(1-phenyl-ethyl)amino]-6-(4-hydroxy-phenyl)-7H-
pyrrolo[2,3-d]pyrimidine
3-cyano-4-[(3-chloro-4-fluorophenyl)amino]-6-{[4-(N,N-
dimethylamino)-1-oxo-2-buten-1-yl]amino}-7-ethoxy-
quinoline
4-{[3-chloro-4-(3-fluoro-benzyloxy)-phenyl]amino}-6-(5-{
[(2-methanesulphonyl-ethyl)amino]methyl}-furan-2-yl)
quinazoline
4-[(R)-(1-phenyl-ethyl)amino]-6-{[4-((R)-6-methyl-2-oxo-
morpholin-4-yl)-1-oxo-2-buten-1-yl]amino}-7-methoxy-
quinazoline
4-[(3-chloro-4-fluorophenyl)amino]-6-{[4-(morpholin-4-
yl)-1-oxo-2-buten-1-yl]-amino}-7-[(tetrahydrofuran-2-
yl)methoxy]-quinazoline 4-[(3-chloro-4-fluorophenyl)amino]-6-({4-[N,N-to-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5,5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(methoxymethyl)carbonyl]-piperidin-4-yloxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonylmethyl-piperidin-4-yloxy)-7-methoxy-quinazoline 4-[(3-chloro-4-fluoro-phenyl)amino]-6-(cis-4-{N—[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N—[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N—[(morpholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethanesulphonylamino-cyclohexan-1-yloxy)-7-methoxy-quinazoline 4-[(3-chloro-4-fluoro-phenyl)amino]-6-(1-methanesulphonyl-piperidin-4-yloxy)-7-ethoxy-quinazoline 4-[(3-chloro-4-fluoro-phenyl)amino]-6-(1-methanesulphonyl-piperidin-4-yloxy)-7-(2-methoxy-ethoxy)-quinazoline 4-[(3-chloro-4-fluoro-phenyl)amino]-6-[1-(2-methoxy-acetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-(tetrahydropyran-4-yloxy]-7-methoxy-quinazoline 4-[(3-chloro-4-fluoro-phenyl)amino]-6-(cis-4-{N—[(piperidin-1-yl)carbonyl]-N-methyl-amino}-cyclohexan-1-yloxy)-7-methoxy-quinazoline 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline 4-[(3-chloro-4-fluoro-phenyl)amino]-6-{cis-4-[(morpholin-4-yl)carbonylamino-cyclohexan-1-yloxy}-7-methoxy-quinazoline 4-[(3-chloro-4-fluoro-phenyl)amino]-6-{1-[2-(2-oxopyrrolidin-1-yl)ethyl]-piperidin-4-yloxy}-7-methoxy-quinazoline 4-[(3-chloro-4-fluoro-phenyl)amino]-6-f{1-[(morpholin-4-yl)carbonyl]-piperidin-4-yloxy}-7-(2-methoxy-ethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline 4-[(3-ethynyl-phenyl)amino]-6-(1-methanesulphonyl-piperidin-4-yloxy)-7-methoxy-quinazoline 4-[(3-chloro-4-fluoro-phenyl)amino]-6-(1-methyl-piperidin-4-yloxy)-7(2-methoxy-ethoxy)-quinazoline 4-[(3-chloro-4-fluoro-phenyl)amino]-6-(1-isopropyloxycarbonyl-piperidin-4-yloxy)-7-methoxy-quinazoline 4-[(3-chloro-4-fluoro-phenyl)amino]-6-(cis-4-methylamino-cyclohexan-1-yloxy)-7-methoxy-quinazoline 4-[(3-chloro-4-fluoro-phenyl)amino]-6-{cis-4-[N-(2-methoxy-acetyl)-N-methyl-amino]-cyclohexan-1-yloxy}-7-methoxy-quinazoline 4-[(3-ethynyl-phenyl)amino]-6-(piperidin-4-yloxy)-7-methoxy-quinazoline 4-[(3-ethynyl-phenyl)amino]-6-[1-(2-methoxy-acetyl)-piperidin-4-yloxy]-7-methoxy-quinazoline 4-[(3-ethynyl-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(cis-2,6-dimethyl-morpholin-4-yl)carbonyl]-piperidin-4-yloxy}-7-methoxy-quinazoline 4-[(3-chloro-4-fluoro-phenyl)amino]-6-{1-[(2-methyl-morpholin-4-yl)carbonyl]-piperidin-4-yloxy}-7-methoxy-quinazoline 4-[(3-chloro-4-fluoro-phenyl)amino]-6-{1-[(S,S)-(2-oxa-5-aza-bicyclo[2,2,1]hept-5-yl)carbonyl-piperidin-4-yloxy}-7-methoxy-quinazoline 4-[(3-chloro-4-fluoro-phenyl)amino]-6-{1-[(N-methyl-N2-methoxyethyl-amino)carbonyl]-piperidin-4-yloxy}-7-methoxy-quinazoline 4-[(3-chloro-4-fluoro-phenyl)amino]-6-(1-ethyl-piperidin-4-yloxy)-7-methoxy-quinazoline 4-[(3-chloro-4-fluoro-phenyl)amino]-6-{1-[(2-methoxyethyl)carbonyl]-piperidin-4-yloxy}-7-methoxy-quinazoline 4-[(3-chloro-4-fluoro-phenyl)amino]-6-{1-[(3-methoxypropyl-amino)-carbonyl]-piperidin-4-yloxy}-7-methoxy-quinazoline 4-[(3-chloro-4-fluoro-phenyl)amino]-6-[cis-4-(N-methanesulphonyl-N-methyl-amino)-cyclohexan-1-yloxy]-7-methoxy-quinazoline 4-[(3-chloro-4-fluoro-phenyl)amino]-6-[cis-4-(N-acetyl-N-methyl-amino)-cyclohexan-1-yloxy]-7-methoxy-quinazoline 4-[(3-chloro-4-fluoro-phenyl)amino]-6-(trans-4-methylamino-cyclohexan-1-yloxy)-7-methoxy-quinazoline 4-[(3-chloro-4-fluoro-phenyl)amino]-6-[trans-4-(N-methanesulphonyl-N-methyl-amino)-cyclohexan-1-yloxy]-7-methoxy-quinazoline 4-[(3-chloro-4-fluoro-phenyl)amino]-6-(trans-4-dimethylamino-cyclohexan-1-yloxy)-7-methoxy-quinazoline 4-[(3-chloro-4-fluoro-phenyl)amino]-6-(trans-4-{N—[(morpholin-4-yl)carbonyl]-N-methyl-amino}-cyclohexan-1-yloxy)-7-methoxy-quinazoline 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline 4-[(3-chloro-4-fluoro-phenyl)amino]-6-(1-methanesulphonyl-piperidin-4-yloxy)-7-methoxy-quinazoline 4-[(3-chloro-4-fluoro-phenyl)amino]-6-(1-cyano-piperidin-4-yloxy)-7-methoxy-quinazoline optionally, in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorphenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

It is also possible to use inhalable macromolecules, as disclosed in European Patent Application EP 1 003 478 A1 or Canadian Patent Application CA 2297174 A1.

In addition, the compounds may come from the groups of ergot alkaloid derivatives, the triptans, the CGRP-inhibitors, the phosphodiesterase-V inhibitors, optionally in the form of the racemates, enantiomers or diastereomers thereof, optionally in the form of the pharmacologically acceptable acid addition salts, the solvates and/or hydrates thereof.

Examples of ergot alkaloid derivatives are dihydroergotamine and ergotamine.

What is claimed is:

1. Atomizer for delivering a formulation from a reservoir having a plurality of receptacles disposed in an annular arrangement, each containing a dose of the formulation, the atomizer comprising:
   a delivery device for delivering the formulation from the receptacles,
   an energy store which surrounds the delivery device,
   an end-piece or mouthpiece for delivering the formulation as an aerosol to a user, and
- a manually movable cover associated with the end-piece or mouthpiece,
- wherein in a closed state of the cover said cover covers the mouthpiece or end-piece and in an opened state of the cover the mouthpiece or end-piece is freely accessible, wherein the atomizer comprises the following features:
- the cover is coupled to the energy store such that, by at least one of opening and closing of the cover energy is generated and stored in the energy store so that a delivery medium can be put under pressure by the energy store,
- wherein the atomizer is constructed so that the pressure in the energy store is released in order to deliver the formulation by means of the delivery medium, and
- wherein the energy store is arranged inside of the annular arrangement of receptacles.

2. Atomizer according to claim 1, wherein the energy store is a spring store, and wherein the atomizer is constructed so that the spring store is put under tension for storing of energy.

3. Atomizer according to claim 1, wherein the atomizer is constructed so that the formulation can be delivered and atomized by means of a delivery medium being at least one of taken in and put under pressure.

4. Atomizer according to claim 1, wherein the atomizer is constructed so that, by opening or closing the cover, a transporting device is actuated that causes the reservoir to be advanced by one receptacle.

5. Atomizer according to claim 1, wherein the atomizer is constructed so that, by opening the cover, a connecting device is actuated in order to at least one of connect the next receptacle to the delivery device for atomization of the respective dose and open the receptacle.

6. Atomizer according to claim 1, wherein the atomizer is constructed so that the cover is movable at least one of transversally to a direction of delivery of the end-piece or mouthpiece, tangentially to a housing and along a periphery of the atomizer.

7. Atomizer according to claim 1, wherein the cover extends substantially peripherally along a circumferential section of the atomizer.

8. Atomizer according to claim 1, wherein the delivery device comprises or forms a pump.

9. Atomizer according to claim 8, wherein the pump is an air pump.

10. Atomizer according to claim 1, wherein the delivery device comprises a bellows for conveying the delivery medium.

11. Atomizer according to claim 1, wherein the atomizer comprises a transporting device for stepwise advancing of the reservoir to empty the receptacles one after another so as to atomize the respective dose.

12. Atomizer according to claim 11, wherein the reservoir has teeth in which the transporting device engages for moving or rotating of the reservoir in order to advance the receptacles.

13. Atomizer according to claim 1, wherein the reservoir is constructed as a rigid ring.

14. Atomizer according to claim 1, wherein the end-piece or mouthpiece for delivering the formulation is at least one of fixed and radially directed.

15. Atomizer according to claim 1, wherein the atomizer has a flat disc-shaped construction.

16. Atomizer according to claim 1, wherein the atomizer has a central axially pressable actuating element for triggering a delivery of a dose of the formulation.

17. Atomizer according to claim 1, wherein the atomizer has a counter for indicating one of the doses already dispensed and those still available.

18. Atomizer according to claim 1, wherein the atomizer has a clock device for providing a reminder to use the atomizer.

19. Atomizer according to claim 1, wherein the atomizer is constructed as a portable inhaler for medicinal aerosol therapy.

20. Atomizer according to claim 1, further comprising a housing, wherein the energy store is arranged in the center of the housing.

21. Atomizer according to claim 1, wherein the delivery medium is air.

22. Atomizer for delivering a formulation from a reservoir having a plurality of annularly arranged receptacles, each of which contains a dose of the formulation, the atomizer comprising:

a delivery device having a pump and an energy store for delivering the formulation from the receptacles, an end-piece or mouthpiece for delivering the formulation as an aerosol to a user, and a manually movable cover associated with the end-piece or mouthpiece, wherein in a closed state of the cover said cover covers the end-piece or mouthpiece and in an opened state of the cover the end-piece or mouthpiece is freely accessible for delivering the formulation, wherein the atomizer comprises the following features:

the cover is coupled to an energy store such that, by at least one of opening and closing of the cover energy is generated and stored in the energy store so that a delivery medium can be put under pressure by the energy store, and a connecting device to connect a next receptacle to the delivery device, wherein the atomizer is constructed so that the pressure in the energy store is released in order to deliver the formulation by means of the delivery medium, and wherein the delivery device is movable in a radial manner.

23. Atomizer according to claim 22, wherein at least one of the delivery device and the connecting device is slidable by means of a sliding guide.

24. Atomizer according to claim 22, wherein the atomizer has a disc-shaped body, and wherein the cover is mounted to move in a circumferential direction along a perimeter of the disc-shaped body between said open state and said closed state.

25. Atomizer according to claim 22, the delivery device and connecting device are moveable together in a radial manner.

26. Atomizer according to claim 22, wherein the pump is an air pump.

27. Atomizer according to claim 22, wherein the delivery medium is air.

* * * * *